(12) United States Patent
Kamei et al.

(10) Patent No.: US 7,056,682 B2
(45) Date of Patent: Jun. 6, 2006

(54) IMMUNOASSAY METHOD AND IMMUNOASSAY REAGENT KIT TO BE USED THEREIN

(75) Inventors: Akihito Kamei, Yawata (JP); Noriko Kenjo, Hirakata (JP); Tatsuro Kawamura, Kyotanabe (JP); Mahito Hirai, Kyotanabe (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 92 days.

(21) Appl. No.: 10/474,755

(22) PCT Filed: Dec. 27, 2002

(86) PCT No.: PCT/JP02/13871

§ 371 (c)(1),
(2), (4) Date: Oct. 10, 2003

(87) PCT Pub. No.: WO03/056333

PCT Pub. Date: Jul. 10, 2003

(65) Prior Publication Data

US 2004/0121417 A1    Jun. 24, 2004

(30) Foreign Application Priority Data

Dec. 27, 2001  (JP)  ............................. 2001-396381

(51) Int. Cl.
*G01N 33/53* (2006.01)
(52) U.S. Cl. .................. 435/7.1; 435/7.92; 436/501; 436/164
(58) Field of Classification Search .............. 435/7.1, 435/7.92–7.94, 975; 436/501, 518, 164, 436/524, 808
See application file for complete search history.

(56) References Cited

U.S. PATENT DOCUMENTS

| 4,672,045 A | 6/1987 | Tsutsui et al. |
| 5,272,258 A | 12/1993 | Siegel et al. |

(Continued)

FOREIGN PATENT DOCUMENTS

JP    02-61561    3/1990

(Continued)

OTHER PUBLICATIONS

Grant, Julius, Hackh's Chemical Dictionary, 3rd Edition, McGraw-Hill Book company, Inc., p. 653.*

(Continued)

*Primary Examiner*—Long V. Le
*Assistant Examiner*—Gary W. Counts
(74) *Attorney, Agent, or Firm*—McDermott Will & Emery LLP

(57) ABSTRACT

In step St1 shown in FIG. 1, a reaction system including a sample for which the content of a subject substance is to be measured, a specific-binding substance specifically binding to the subject substance, and phthalic acid or phthalate salt is constructed. The pH of the reaction system is set at less than 7. When the subject substance is an antigen, the specific-binding substance is an antibody. In reverse, when the subject substance is an antibody, the specific-binding substance is an antigen. In step St2 in FIG. 1, an optical property of the reaction system is measured. When agglutinate complexes are produced in the step St1, the reaction system becomes turbid, causing a change in scattered light intensity, transmitted light amount and the like. Therefore, by measuring the scattered light intensity, the transmitted light amount or the like, the degree of turbidity of the reaction system can be estimated.

12 Claims, 10 Drawing Sheets

```
Construct a reaction system including a
sample solution, a specific-binding substance
specifically binding to a subject substance,     ~ St1
and phthalic acid or phthalate salt

|
                      v

Measure an optical property of
           the reaction system              ~ St2
```

U.S. PATENT DOCUMENTS

| | | | |
|---|---|---|---|
| 5,358,852 A * | 10/1994 | Wu | 435/7.94 |
| 6,143,247 A * | 11/2000 | Sheppard et al. | 422/63 |
| 6,617,123 B1 * | 9/2003 | Smith | 435/19 |
| 2001/0005585 A1 * | 6/2001 | Ashihara et al. | 435/7.95 |
| 2003/0082589 A1 * | 5/2003 | Chan et al. | 435/6 |
| 2003/0129296 A1 * | 7/2003 | Kelso | 427/2.1 |

FOREIGN PATENT DOCUMENTS

| | | |
|---|---|---|
| JP | 6-82450 | 3/1994 |
| JP | 6-213890 A | 8/1994 |
| JP | 10-332694 | 12/1998 |
| JP | 11-344494 | 12/1999 |

OTHER PUBLICATIONS

Takahiro Hamasaki, "Edta Sonzaiji No Shihan Kokessei No Crp Eno Ketsugo Kassei No Teika", The Japanese Journal of Clinical Pathology, Feb. 23, 1984, vol. 32, No. 2, pp. 223 to 224.

* cited by examiner

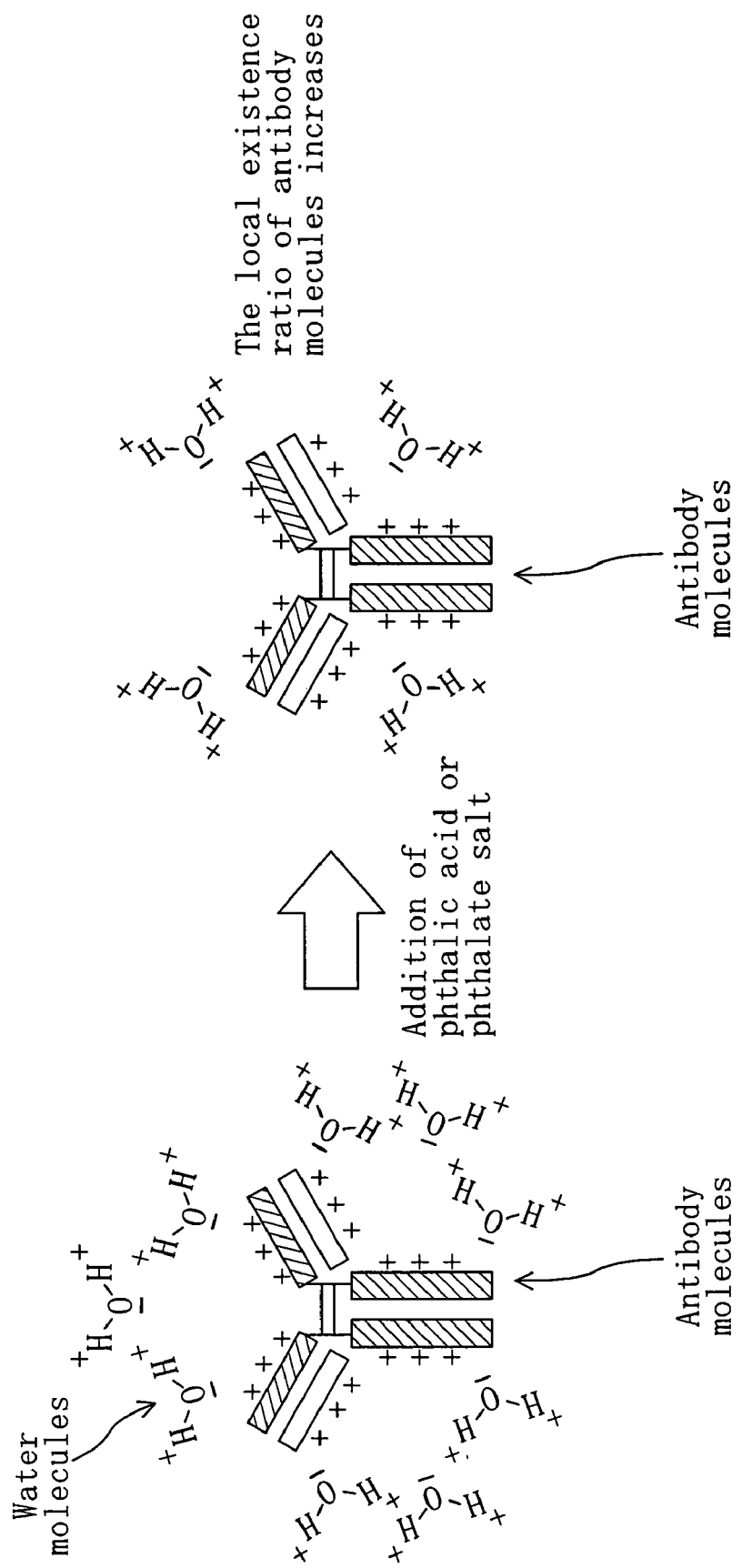

—●— 0.05M potassium hydrogen phthalate, 4 wt.% PEG 6000, pH 4.5
—✕— 0.05M MOPS, 4 wt.% PEG 6000, pH 7.4

IMMUNOASSAY METHOD AND IMMUNOASSAY REAGENT KIT TO BE USED THEREIN

TECHNICAL FIELD

The present invention relates to an immunoreaction measurement method capable of measuring the content of an antibody or an antigen as a subject substance in a sample, and a reagent kit for immunoreaction measurement used for this method.

BACKGROUND ART

In the medical field, for diagnosis of various diseases and examination of progress of the condition of a disease, measurement of the content of a protein distinctive to a disease existing in a human bodily fluid is widely conducted. For the measurement of the content of a protein, immunoreaction measurement methods, mainly utilizing reaction of an antibody specifically recognizing a target protein as an antigen (antigen-antibody reaction), is in widespread use. At present, immunoreaction measurement methods utilizing various principles have been developed.

Among others, measurement methods such as immunonephelometry, immunoturbidimetry and slide agglutination are well known, in which agglutinates of antigen-antibody complexes (hereinafter, simply called agglutinate complexes) formed by antigen-antibody reaction are detected. These measurement methods are employed in the state that an antigen and an antibody are dispersed uniformly in a solution, which are therefore collectively called "homogeneous immunoreaction measurement methods".

In the antigen-antibody reaction, the reaction system becomes turbid with formation of agglutinate complexes. The degree of turbidity generated in the reaction system with formation of agglutinate complexes depends on the amount of the antigen and the amount of the antibody. Immunonephelometry and immunoturbidimetry are methods utilizing this fact, in which the degree of turbidity generated in the reaction system is optically measured and the amount of the antigen or the amount of the antibody is computed from the measured value.

The degree of turbidity generated in the reaction system is measured based on the amount of light scattered in the reaction system for immunonephelometry, or based on the amount of transmitted light decreasing due to scattering in the reaction system for immunoturbidimetry. In general, the same reaction system can be used for measurement by immunonephelometry and measurement by immunoturbidimetry. In other words, a reaction system usable for measurement by either immunonephelometry or immunoturbidimetry can be used for measurement by the other method. Slide agglutination is a method in which a solution in a reaction system having turbidity is collected on a glass slide or the like and the degree of turbidity in the reaction system is determined by visual observation and the like. The same reaction system as that used for immunonephelometry and immunoturbidimetry can be used for the slide agglutination method.

PROBLEM TO BE SOLVED

In the conventional homogeneous immunoreaction measurement methods described above, use of various additives has been attempted to facilitate antigen-antibody reaction to thereby achieve high sensitive measurement of a trace component. In a well-known example, a water soluble polymer such as polyethylene glycol, dextran, polyvinyl pyrrolidone and polyvinyl chloride is mixed in a reaction system, to facilitate formation of agglutinate complexes due to antigen-antibody reaction. This shortens the reaction time and improves the measured value, to thereby enhance the measurement sensitivity. Among the water soluble polymers mentioned above, polyethylene glycol is known to be high in the effect of shortening the reaction time and improving the measured value at a comparatively low concentration. In particular, addition of polyethylene glycol (PEG) having an average molecular weight of 6,000 to have a concentration of 2 to 6 wt. % in a reaction system is widely known. It is especially considered that addition of polyethylene glycol having an average molecular weight of 6,000 to have a concentration of 4 wt. % in a reaction system is small in generation of non-specific turbidity other than the turbidity due to agglutinate complexes and thus high in the above effect.

The effect of a water soluble polymer of facilitating antigen-antibody reaction generally tends to be greater as the molecular weight of the water soluble polymer is larger and the concentration of the water soluble polymer is higher (see Automated Immunoanalysis Part 1, ed. by Ritchie, pp. 67–112 (1978)).

In measurement of antigen-antibody reaction, as the signal intensity (that is, the measured value) that depends on the degree of the antigen-antibody reaction (that is, the concentration of the antigen) is higher, a good S/N ratio can be maintained and stable measurement can be ensured with more certainty. However, when a water soluble polymer is added in a high concentration, or a water soluble polymer having a high molecular weight is added, to a reaction system, as conventionally done, in an attempt of further facilitating the antigen-antibody reaction to obtain the above effect, the viscosity of a solution in the reaction system in which the water soluble polymer is dissolved increases. This causes a problem of making handling of the solution during measurement operation difficult. As a result, high signal intensity (that is, measured value) may not be obtained and thus stable measurement may be difficult in some cases.

DISCLOSE OF THE INVENTION

In view of the situation described above, an object of the present invention is providing an immunoreaction measurement method capable of improving the measured value easily to obtain high measurement sensitivity, and a reagent kit for immunoreaction measurement used for this method.

The immunoreaction measurement method of the present invention is a method for measuring the content of a subject substance in a sample, including the steps of (A) constructing a reaction system including the sample, a specific-binding substance specifically binding to the subject substance and phthalic acid or phthalate salt; and (B) measuring an optical property of the reaction system, wherein in the step (A), the pH of the reaction system is set at less than 7, and the combination of the subject substance and the specific-binding substance is a combination of an antigen and an antibody.

According to the immunoreaction measurement method of the present invention, the measured value of an optical property of the reaction system can be improved. Also, the phthalic acid or phthalate salt used in the present invention, which is a low molecular-weight substance, does not increase the viscosity of the reaction system, and thus handling of the solution during measurement operation is easy.

The optical property may be a scattered light intensity or a transmitted light amount.

In the step (A), the reaction system may further include a buffering agent.

In the step (A), the pH of the reaction system is preferably set in a range of 4.5 to 5.5.

In the step (A), the concentration of the phthalic acid or phthalate salt in the reaction system is preferably 0.2 M or less.

The phthalate salt is preferably potassium hydrogen phthalate.

The reaction system may include 2 to 6 wt. % polyethylene glycol.

The subject substance may be an antigen having a structure of holding metal ions inside, and the specific-binding substance may be an antibody specifically binding to the antigen that does not hold the metal ions.

The subject substance may be human C-reactive protein.

The subject substance may be an antigen having a structure of holding metal ions inside, the specific-binding substance may be a polyclonal antibody, and in the step (A), the reaction system may further include the metal ions.

The subject substance may be human C-reactive protein.

The subject substance may be an antigen, and the specific-binding substance may be a monoclonal antibody capable of binding to a plurality of binding sites of the antigen.

The subject substance may be human C-reactive protein.

The reagent kit for immunoreaction measurement of the present invention is a reagent kit for immunoreaction measurement for measuring the content of a subject substance in a sample, including: a specific-binding substance specifically binding to the subject substance; and phthalic acid or phthalate salt wherein the pH of a reaction system is set to be less than 7 when the reaction system including the sample, the specific-binding substance and the phthalic acid or phthalate salt is constructed and, wherein the combination of the subject substance and the specific-binding substance is a combination of an antigen and an antibody.

According to the reagent kit for immunoreaction measurement of the present invention, the measured value of an optical property of the reaction system can be improved. Also, the phthalic acid or phthalate salt used in the present invention, which is a low molecular-weight substance, does not increase the viscosity of the reaction system, and thus handling of the solution during measurement operation is easy.

The pH of the reaction system is preferably set in a range of 4.5 to 5.5.

The reagent kit is preferably prepared so that the concentration of the phthalic acid or phthalate salt in the reaction system is 0.2 M or less.

The phthalate salt is preferably potassium hydrogen phthalate.

The reagent kit may further include polyethylene glycol, and may be prepared so that the concentration of the polyethylene glycol in the reaction system is in a range of 2 to 6 wt. %.

The subject substance may be an antigen having a structure of holding metal ions inside, and the specific-binding substance may be an antibody specifically binding to the antigen that does not hold the metal ions.

The antibody may be an antihuman C-reactive protein antibody.

The reagent kit may further include a metal compound supplying metal ions, the subject substance may be an antigen having a structure of holding metal ions inside, the antigen may have a structure of holding the metal ions inside, and the specific-binding substance may be a polyclonal antibody.

The antibody may be an antihuman C-reactive protein antibody.

The subject substance may be an antigen, and the specific-binding substance may be a polyclonal antibody capable of binding to a plurality of binding sites of the antigen.

The monoclonal antibody may be an antihuman C-reactive protein antibody.

The specific-binding substance and the phthalic acid or phthalate salt may be in a mixed state.

BRIEF DESCRIPTION OF THE DRAWINGS

FIG. 2 is a diagrammatic view demonstrating the inventors' presumption on the reaction mechanism according to the present invention.

BEST MODE FOR CARRYING OUT THE INVENTION

As described before, in an immunoreaction measurement method for measuring the content of a subject substance to be measured in a sample, antigen-antibody reaction involving the subject substance is allowed to occur, and the amount of the subject substance is computed from the measured value of an optical property of a reaction system after the reaction.

When conducting the measurement described above, the present inventors found out an immunoreaction measurement method and a reagent kit for immunoreaction measurement capable of obtaining a high measured value (that is, high measurement sensitivity). Moreover, it was found that the immunoreaction measurement method and the reagent kit for immunoreaction measurement found out by the present inventors could also ease a zone phenomenon occurring in an antigen-excess region.

Figure 1:
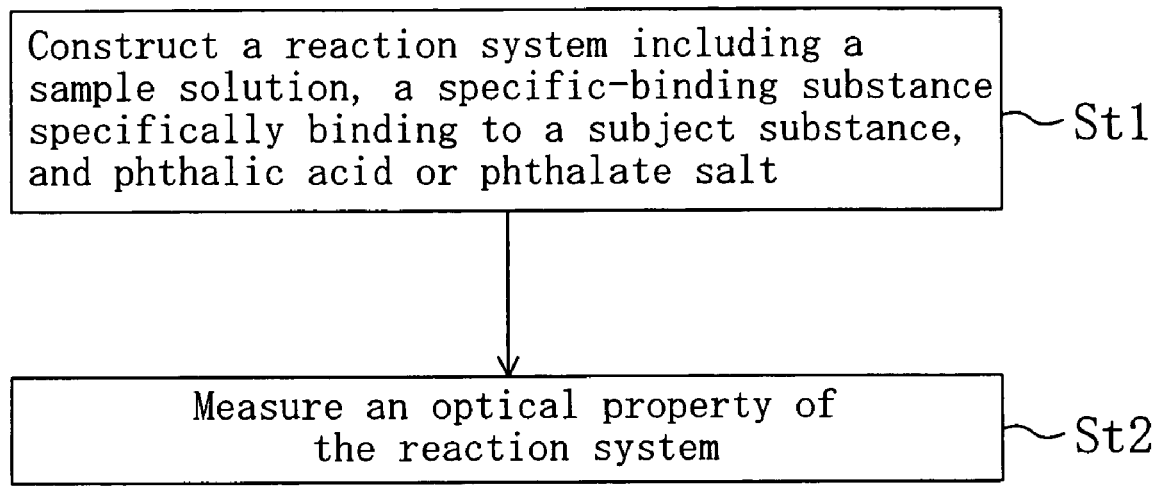
FIG. 1 is a flowchart showing steps of an immunoreaction measurement method of an embodiment of the present invention.

Hereinafter, an embodiment of the present invention will be described with reference to FIG. 1. FIG. 1 is a flowchart showing steps of an immunoreaction measurement method of this embodiment. Note that herein the wording "measured value" is used as expressing the same meaning as the signal intensity unless otherwise specified.

First, in step St1 shown in FIG. 1, constructed is a reaction system including a sample for which the content of a subject substance is to be measured, a specific-binding substance specifically binding to the subject substance, and phthalic acid or phthalate salt. The pH of the reaction system is set at less than 7. When the subject substance is an antigen, the specific-binding substance is an antibody. In reverse, when the subject substance is an antibody, the specific-binding substance is an antigen.

By the above construction, if the subject substance is contained in the sample, agglutinate complexes are formed due to the antigen-antibody reaction between the subject substance and the specific-binding substance. If the subject substance is not contained in the sample, there is no formation of agglutinate complexes due to the antigen-antibody reaction between the subject substance and the specific-binding substance.

In step St2 shown in FIG. 1, an optical property of the reaction system is measured. When agglutinate complexes are formed in the step St1, the reaction system becomes turbid causing a change in scattered light intensity, transmitted light amount and the like. Therefore, by measuring the scattered light intensity, the transmitted light amount or the like, the degree of turbidity of the reaction system can be estimated. In this measurement, it is preferred to measure an optical change amount of the reaction system, that is, an amount of change in scattered light intensity or transmitted light amount, using a reference obtained by excluding the specific-binding substance from the reaction system. Otherwise, a reference obtained by excluding the sample from the reaction system may be used.

By executing the steps described above, it is possible to improve the measured value of an optical property of the reaction system caused by the agglutinate complexes formed by the antigen-antibody reaction. Therefore, according to the immunoreaction measurement method of this embodiment, the amount of the object substance can be measured with high sensitivity. The reason why this effect is obtained is unknown at the current stage, but the present inventors presume this effect is obtained for the following reason, which will be described with reference to FIG. 2.

Phthalic acid and phthalate salt are considered existing in an aqueous solution as phthalic acid or phthalic acid ions. Phthalic acid and phthalic acid ions, which have a polarity, are considered having a nature of easily attracting water molecules in the aqueous solution. By adding such phthalic acid or phthalate salt to the reaction system, water molecules are considered gathering around the phthalic acid and phthalic acid ions. Therefore, the amount of water molecules existing around antibody molecules significantly decreases as shown in FIG. 2, and thus the local existence ratio of antibody molecules increases. This presumably increases collision between the antigen and the antibody, and thus facilitates antigen-antibody reaction. As a result, presumably, formation of agglutinate complexes is facilitated, and thus the measured value of an optical property of the reaction system improves.

As described before, in the conventional method involving adding a water soluble polymer, it is necessary to add a water soluble polymer in a higher concentration or a water soluble polymer having a higher molecular weight, to improve the measured value, maintain a good S/N ratio and ensure stable measurement. This causes a problem of increasing the viscosity of the solution and thus making handling of the solution during analysis operation difficult. In this embodiment, however, phthalic acid or phthalate salt, which is a low molecular-weight substance, does not increase the viscosity of the solution, and thus handling of the solution during measurement operation is easy.

Figure 3A:
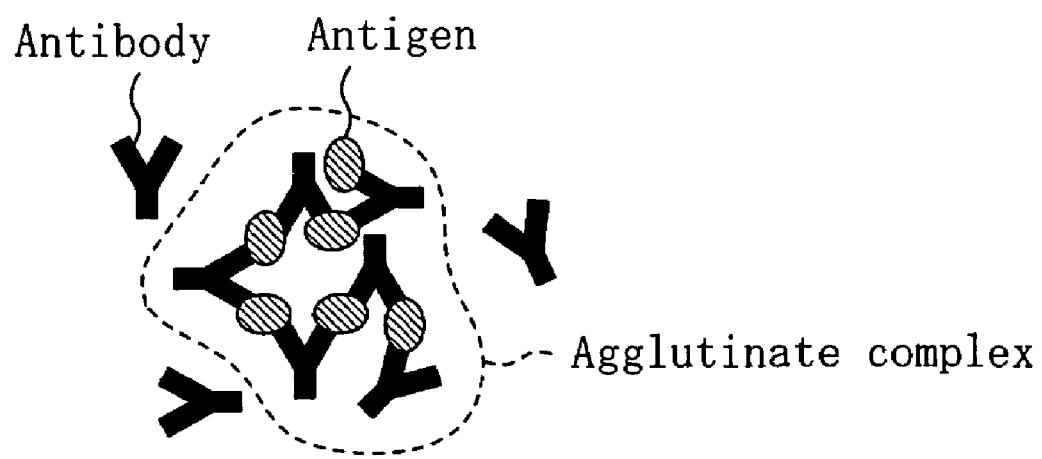
FIGS. 3(a) and 3(b) are views diagrammatically illustrating how an antigen and an antibody react in a reaction system in a homogeneous immunoreaction measurement method.
Figure 3B:
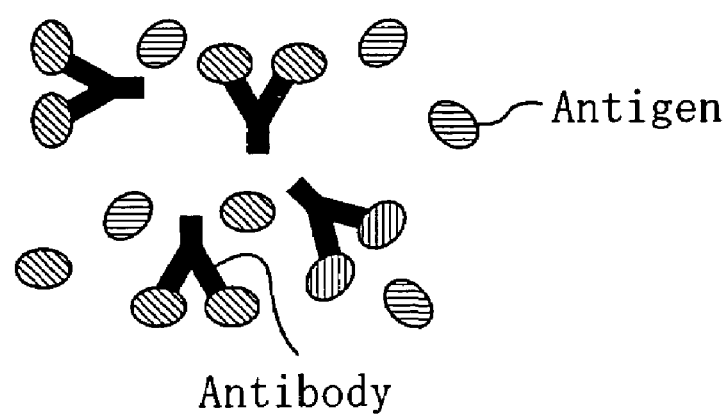

In the immunoreaction measurement method of this embodiment, the zone phenomenon occurring when an antigen exists in an excessive amount can be eased. This will be described with reference to FIGS. 3(a) and 3(b). FIGS. 3(a) and 3(b) are views diagrammatically illustrating how an antigen and an antibody react in a reaction system in a homogeneous immunoreaction measurement method.

In general, in a homogeneous immunoreaction measurement method, occurrence of a phenomenon called the zone phenomenon is known. As shown in FIG. 3(a), an agglutinate complex as a huge molecular chain including an antibody and an antigen alternately binding to each other is normally formed in a homogeneous immunoreaction measurement method. The zone phenomenon is a phenomenon in which an agglutinate complex is less easily formed when the antigen exists in an excessive amount with respect to the antibody, as shown in FIG. 3(b), compared with the amount in an equivalent region within which the antigen and the antibody form the maximum amount of agglutinate complexes. As for the binding reaction between a multivalent antibody and a divalent or higher-valent antigen, the lattice theory by Heidelberger and others is famous, details of which is described in Fundamental Immunology, ed. by William E. Paul, 1984 (Japanese translation, Kiso Menekigaku, translated by Tomio Tada, pp.714–716 (1987)).

In the antigen and antibody concentration ranges free from the zone phenomenon, an agglutinate complex is formed as a huge molecular chain in which the antibody and the antigen bind to each other alternately as shown in FIG. 3(a). When the antibody concentration is constant, the amount and size of agglutinate complexes increase with increase of the antigen concentration. Therefore, by measuring the amount and size of agglutinate complexes as an optical change amount, the antigen concentration can be measured quantitatively. The agglutinate complexes are large enough to allow confirmation of their existence by the naked eye as turbidity and agglutinates in the solution, depending on the antibody and antigen concentrations. Therefore, qualitative judgment by visual observation and the like is also possible.

In an actual homogeneous immunoreaction measurement method, the antigen concentration is measured using an antibody in many cases. Also, in many cases, the measured value gives an important indication when the antigen concentration is high than when it is low. However, if the antigen exists in an excessive amount with respect to the antibody, binding sites of the antibody are saturated with the antigen in a large amount as shown in FIG. 3(b), and thus formation of agglutinate complexes becomes difficult. This makes it difficult to distinguish the results of the antigen-antibody reaction between the case that the antigen is in a low concentration and the case that the antigen is excessive. This causes a problem that correct quantification and judgment according to the antigen concentration may not be attained, or that the measurable concentration range is limited to attain correct quantification and judgment according to the antigen concentration. This zone phenomenon occurring when an antigen exists in an excessive amount often becomes a cause of a trouble arising in a homogeneous immunoreaction measurement method.

According to the immunoreaction measurement method of this embodiment, the zone phenomenon occurring when an antigen exists in an excessive amount with respect to an antibody can be eased. The reason is that formation of agglutinate complexes is facilitated by addition of phthalic acid or phthalate salt to the reaction system as described above.

Also, according to the immunoreaction measurement method of this embodiment, with the easing of the zone phenomenon, drop of the measured value for the subject substance in a high concentration is reduced. This enables widening of the measurable concentration range within which the content of the subject substance can be measured precisely.

Hereinafter, the respective steps will be described in detail.

In the step St1, as described above, constructed is a reaction system including a subject substance, a specific-binding substance specifically binding to the subject substance, and phthalic acid or phthalate salt. Both phthalic acid and phthalate salt may be included in the reaction system. Naturally, either phthalic acid or phthalate salt may be included in the reaction system.

In the step St1, the phthalic acid or phthalate salt preferably provides buffering capability to set the pH of the reaction system at less than 7. This eliminates the necessity of adding another buffering agent for setting the pH of the reaction system at less than 7, and yet enables efficient achievement of the effects of improving the measured value and easing the zone phenomenon described above. To provide the buffering capability to the reaction system by the phthalic acid or phthalate salt, the concentration of the phthalic acid or phthalate salt is preferably 0.01 M or more.

In the immunoreaction measurement method of this embodiment, the pH of the reaction system in the step St1 is preferably in the range of 4.5 to 5.5, more preferably in the range of 4.5 to 5.3, further more preferably in the range of 4.5 to 5.0. Within the above pH range, the effect of improving the measured value is high, and also the effect of easing the zone phenomenon is high. Most preferably, the pH of the reaction system should be adjusted to 4.5.

In the immunoreaction measurement method of this embodiment, the concentration of the phthalic acid or phthalate salt in the reaction system in the step St1 is preferably 0.2 M or less. With this concentration, the effect of improving the measured value is higher, and also the effect of easing the zone phenomenon is higher. To further increase these effects, it is more preferred to set the concentration of the phthalic acid or phthalate salt in the reaction system at 0.1 M or less. Particularly, to significantly increase these effects, it is further more preferred to set the concentration of the phthalic acid or phthalate salt in the reaction system at about 0.1 M.

In the step St1, another buffering agent may additionally be added to the reaction system. The buffering agent usable for the immunoreaction measurement method of this embodiment is one known in the art, including, for example, phosphoric acid type buffering agents such as sodium dihydrogen phosphate and disodium hydrogen phosphate, sodium acetate, sodium cacodylate, 2-(N-morpholino) ethanesulfonic acid and succinic acid. In the case of adding a buffering agent, the amount of the buffering agent to be included in the reaction system may be appropriately adjusted depending on the kind of the buffering agent used, the amount of the sample (analyte) containing the subject substance, the way of supply of the antibody or the antigen against the antigen or the antibody as the subject substance in the reaction system, and the like.

Examples of the phthalic acid and phthalate salt used for the immunoreaction measurement method of this embodiment include phthalic acid, phthalic anhydride, potassium hydrogen phthalate, potassium phthalate, disodium phthalate, ammonium phthalate and copper (II) phthalate. These are all on the market and thus easily available. These may be used alone or in combination. Among others, potassium hydrogen phthalate is particularly preferred as the phthalate salt used for the immunoreaction measurement method and the reagent kit for immunoreaction measurement of this embodiment, for the reasons that the water solubility thereof is high and that the pH of its aqueous solution when dissolved is around 4.0.

The phthalic acid includes isomers, that is, o-phthalic acid, m-phthalic acid and p-phthalic acid (terephthalic acid). In this embodiment, mixtures of o-phthalic acid, m-phthalic acid and p-phthalic acid may be used. Use of o-phthalic acid alone, which is high in water solubility, is most preferred. In use of phthalate salt, also, as in use of phthalic acid, mixtures of m-phthalate salt, p-phthalate salt and p-phthalate salt may be used. Use of o-phthalate salt alone, which is high in water solubility, is most preferred.

In the immunoreaction measurement method of this embodiment, another arbitrary component known in the art may be added to the reaction system depending on the use of the reaction system as long as the above effects are obtained. For example, in an application to a homogeneous immunoreaction measurement method such as immunonephelometry, immunoturbidimetry and slide agglutination, polyethylene glycol (PEG) may be added to the reaction system in the immunoreaction measurement method of the present invention. The content thereof is preferably 2 to 6 wt. %, more preferably 4 wt. %, as the concentration in the reaction system, because with this concentration, non-specific agglutination is small and the effect of improving the measurement sensitivity is high.

To reduce non-specific turbidity caused by self-agglutination of the antigen or the antibody, a surfactant such as Tween 20, octylglucoside, sodium lauryl sulfate (SDS), sucrose monolaurate and CHAPS may be added to the reaction system in this embodiment. The content of such a surfactant in the reaction system is preferably 0.3% (w/v) or less, more preferably 0.1% (w/v) or less in this embodiment, because with this content, the antigen-antibody reaction is less blocked.

In the step St2 of the immunoreaction measurement method of this embodiment, the method adopted for the measurement of an optical property of the reaction system is not specifically limited. In particular, however, a higher effect is expected by adopting a homogeneous immunoreaction measurement method such as immunonephelometry, immunoturbidimetry and slide agglutination, in which the zone phenomenon may occur. Adoption of immunonephelometry and immunoturbidimetry, in which methods use of an automatic measurement apparatus is widespread, is particularly preferred because the step required for judgment of the zone phenomenon can be curtailed or simplified.

In the immunoreaction measurement method of this embodiment, the antigen-antibody complexes are preferably agglutinate complexes. In the step St2, the agglutinate complexes are preferably detected by measuring an optical change amount caused by the agglutinate complexes. Further preferably, the optical change amount is the amount of change in scattered light intensity or transmitted light amount.

The immunoreaction measurement method of this embodiment may typically be executed in the following manner. Phthalic acid or phthalate salt is added to a buffer solution that contains a buffering agent to keep the pH of the reaction system acidic, preferably at 4.5 to 5.5, more preferably at 4.5. The phthalic acid or phthalate salt is added so that the concentration thereof during the antigen-antibody reaction is 0.2 M or less, preferably 0.1 M or less, particularly preferably 0.1 M. The phthalic acid or phthalate salt may also serve as the buffering agent. A sample (analyte) for which the content of a subject substance is to be measured and a solution containing a specific-binding substance are sequentially added to and mixed with the above buffer solution, to thereby construct the reaction system. An optical change amount of the reaction system is measured using the sample as the reference.

The way of adding the phthalic acid or phthalate salt, the way of adding a buffering agent to keep the pH of the reaction system acidic, and the way of adjusting the pH of the reaction system are not limited to those described above. For example, the phthalic acid or phthalate salt may be mixed in advance in the solution containing the specific-binding substance so as to satisfy the requirements described above. In addition, a buffering agent may be mixed in the solution.

Next, a reagent kit for immunoreaction measurement used for the immunoreaction measurement method of this embodiment will be described.

The reagent kit for immunoreaction measurement of this embodiment is prepared to include a specific-binding substance specifically binding to a subject substance, phthalic acid or phthalate salt, and a buffering agent for setting the pH of a reaction system including the subject substance, the specific-binding substance and the phthalic acid or phthalate salt at less than 7. The combination of the subject substance and the specific-binding substance is a combination of an antigen and an antibody.

The reagent kit for immunoreaction measurement of this embodiment is added to a sample for which the content of the subject substance is to be measured. By this addition, it is possible to construct the reaction system including the sample for which the content of the subject substance is to be measured, the specific-binding substance specifically binding to the subject substance, and the phthalic acid or phthalate salt. If the subject substance is contained in the sample, agglutinate complexes are formed due to the antigen-antibody reaction between the subject substance and the specific-binding substance. If the subject substance is not contained in the sample, there is no formation of agglutinate complexes due to the antigen-antibody reaction between the subject substance and the specific-binding substance.

Accordingly, by executing the steps shown in FIG. 1 using the reagent kit for immunoreaction measurement of this embodiment, it is possible to improve the measured value of an optical property of the reaction system caused by the agglutinate complexes formed due to the antigen-antibody reaction. In other words, the reagent kit for immunoreaction measurement of this embodiment enables measurement of the amount of the subject substance with high measurement sensitivity. In addition, the phthalic acid or phthalate salt used in this embodiment, which is a low molecular-weight substance, does not increase the viscosity of the solution, and thus handling of the solution during measurement operation is easy.

Moreover, the zone phenomenon occurring when the antigen exists in an excessive amount with respect to the antibody can be eased. With the easing of the zone phenomenon, drop of the measured value for the subject substance in a high concentration is reduced. This enables widening of the measurable concentration range within which the content of the subject substance can be measured precisely.

The reagent kit for immunoreaction measurement of this embodiment may include both phthalic acid and phthalate salt. The phthalic acid or phthalate salt preferably provides buffering capability so that the reaction system in the step St1 is prepared to have a pH less than 7. In other words, the phthalic acid or phthalate salt preferably also serves as a buffering agent.

The reagent kit for immunoreaction measurement of this embodiment may further include another buffering agent. As such a buffering agent, one known in the art may be used, including, for example, phosphoric acid type buffering agents such as sodium dihydrogen phosphate and disodium hydrogen phosphate, sodium acetate, sodium cacodylate, 2-(N-morpholino)ethanesulfonic acid and succinic acid. The amount of the buffering agent may be appropriately adjusted depending on the kind of the buffering agent used, the amount of the sample (analyte) containing the subject substance, the way of supply of the antibody or the antigen against the antigen or the antibody as the subject substance in the reaction system, and the like.

The reagent kit for immunoreaction measurement of this embodiment is preferably prepared so that the pH of the reaction system in the step St1 is in the range of 4.5 to 5.5, more preferably in the range of 4.5 to 5.3, further more preferably in the range of 4.5 to 5.0. Within the above pH range, the effect of improving the measured value is high, and the effect of easing the zone phenomenon is high. In particular, the reagent kit is preferably prepared so that the pH of the reaction system is about 4.5.

The reagent kit for immunoreaction measurement of this embodiment is preferably prepared so that the concentration of the phthalic acid or phthalate salt in the reaction system in the step St1 is 0.2 M or less. With this concentration, the effect of improving the measured value is higher, and the effect of easing the zone phenomenon is higher. To further increase these effects, it is more preferred to prepare the reagent kit so that the concentration of the phthalic acid or phthalate salt in the reaction system is 0.1 M or less.

Particularly, to significantly increase these effects, it is further more preferred to prepare the reagent kit so that the concentration of the phthalic acid or phthalate salt in the reaction system is about 0.1 M.

Examples of the phthalic acid and phthalate salt included in the reagent kit for immunoreaction measurement of this embodiment include phthalic acid, phthalic anhydride, potassium hydrogen phthalate, potassium phthalate, disodium phthalate, ammonium phthalate and copper (II) phthalate. These are all on the market and thus easily available. These may be used alone or in combination. Among others, potassium hydrogen phthalate is particularly preferred as the phthalate salt used for the immunoreaction measurement method and the reagent kit for immunoreaction measurement of this embodiment, for the reasons that the water solubility thereof is high and that the pH of its aqueous solution when dissolved is around 4.0.

Phthalic acid includes isomers, that is, o-phthalic acid, m-phthalic acid and p-phthalic acid (terephthalic acid). In this embodiment, mixtures of o-phthalic acid, m-phthalic acid and p-phthalic acid may be used. Use of o-phthalic acid alone, which is high in water solubility, is most preferred. In use of phthalate salt, also, as in use of phthalic acid, mixtures of m-phthalate salt, p-phthalate salt and p-phthalate salt may be used. Use of o-phthalate salt alone, which is high in water solubility, is most preferred.

Another arbitrary component known in the art may be added to the reagent kit for immunoreaction measurement of this embodiment depending on the use thereof and the like as long as the above effects are obtained. For example, in an application to a homogeneous immunoreaction measurement method such as immunonephelometry, immunoturbidimetry and slide agglutination, polyethylene glycol (PEG) may be added to the reagent kit for immunoreaction measurement of this embodiment. The content thereof is preferably 2 to 6 wt. %, more preferably 4 wt. %, as the concentration in the reaction system, because that with this concentration, non-specific agglutination is small and the effect of improving the measurement sensitivity is high.

To reduce non-specific turbidity caused by self-agglutination of the antigen or the antibody, a surfactant such as Tween 20, octylglucoside, sodium lauryl sulfate (SDS), sucrose monolaurate and CHAPS may be added to the reagent kit for immunoreaction measurement of this embodiment. The content of such a surfactant in the reagent kit for immunoreaction measurement of this embodiment is preferably 0.3% (w/v) or less, more preferably 0.1% (w/v) or less in the reaction system, because with this content, the antigen-antibody reaction is less blocked.

The measurement system to which the reagent kit for immunoreaction measurement of this embodiment is applied is not specifically limited. In particular, however, a higher effect is expected by using a homogeneous immunoreaction measurement method such as immunonephelometry, immunoturbidimetry and slide agglutination, in which the zone phenomenon may occur. Adoption of a measurement method like Immunonephelometry and immunoturbidimetry, in which methods use of an automatic measurement apparatus is widespread, is particularly preferred because the step required for judgment of the zone phenomenon can be curtailed or simplified.

Typically, the reagent kit for immunoreaction measurement of this embodiment can be prepared in the following manner.

A solution containing a specific-binding substance (an antibody in this case) specifically binding to a subject substance (an antigen in this case) may be prepared separately from a solution containing phthalic acid or phthalate salt. The procedure in this case is as follows.

The solution containing phthalic acid or phthalate salt is prepared using a buffering agent so that the pH of the reaction system is kept at less than 7. The solution is preferably prepared so that the pH is in the range of 4.5 to 5.5, more preferably in the range of 4.5 to 5.3, further more preferably in the range of 4.5 to 5.0. Most preferably, the solution is prepared so that the pH of the reaction system is 4.5. The amount of the phthalic acid or phthalate salt and the buffering agent is adjusted so that the concentration of the phthalic acid or phthalate salt in the reaction system is 0.2 M or less, preferably 0.1 M or less, particularly preferably about 0.1 M, and the adjusted amount is dissolved in pure water, to prepare the solution.

The buffering agent and the phthalic acid or phthalate salt may be prepared separately by dissolving them in separate solutions as long as the above requirements are satisfied. Alternatively, a solution containing no buffering agent in which the phthalic acid or phthalate salt serves as the buffering agent may be prepared as long as the above pH range is satisfied.

The solution containing the specific-binding substance may have an arbitrary composition as long as the reaction system satisfies the requirements described above when the solution is mixed with the solution containing the phthalic acid or phthalate salt.

The specific-binding substance and the phthalic acid or phthalate salt may be mixed together in advance. In this case, the solution containing the specific-binding substance may be subjected to dialysis or gel filtration with the prepared solution containing the phthalic acid or phthalate salt, for replacement of low molecular-weight components, so as to satisfy the requirements described above.

The antigen or the antibody as the subject substance in the immunoreaction measurement method and the reagent kit for immunoreaction measurement of this embodiment is not specifically limited, and generally may be any substance that can be measured using antigen-antibody reaction. Examples of such a substance include proteins, nucleic acids, lipid, bacteria, viruses and haptens. Among others, proteins are major subjects to be measured in clinical tests using antigen-antibody reaction. Therefore, when the subject substance is a protein, the immunoreaction measurement method and the reagent kit for immunoreaction measurement of this embodiment can be very suitably adopted. Examples of such proteins include hormones such as luteinizing hormone (LH), follicle-stimulating hormone (FSH) and human chorionic gonadotropin (hCG), various immunoglobulin classes and sub-classes, complement components, markers of various infectious diseases, CRPs, albumins, rheumatoid factors and blood group antigens. In particular, the immunoreaction measurement method and the reagent kit for immunoreaction measurement of this embodiment can be used suitably for measurement of a human albumin or a human C-reactive protein (human CRP) among others as the subject substance.

The phthalic acid and phthalate salt have a chelating function, in which divalent and trivalent metal ions such as $Ca^{2+}$ and $Fe^{3+}$ existing in the reaction system are efficiently taken off. Therefore, when the antigen has a structure of holding metal ions inside, the antibody specifically binding to the antigen should preferably be still able to specifically bind to the antigen in the state that the metal ions have been released therefrom. Using such an antibody, measurement is possible even when the antigen is a substance of which the molecular structure changes due to release of metal ions.

When the antigen has a structure of holding metal ions inside and the molecular structure of the antigen changes due to release of metal ions, the same metal ions as those held by the antigen may be added to the reaction system to allow existence of the metal ions in the reaction system. This suppresses a change in the molecular structure of the antigen due to release of metal ions in the reaction system, allowing the antibody to bind to the antigen to enable the measurement.

The amount of metal ions added may be determined based on the chelating capability of the phthalic acid or phthalate salt used, the concentration thereof, the capability of holding metal ions of the antigen and the like.

An example of the antigen having a molecular structure capable of holding metal ions is CRP, which changes in structure depending on the presence or absence of $Ca^{2+}$. Therefore, in the case that the antigen used for the immunoreaction measurement method and the reagent kit for immunoreaction measurement of this embodiment is human CRP, that a goat antihuman CRP polyclonal antibody including an antibody that does not bind to human CRP having no $Ca^{2+}$ is used as the antibody, and that phthalic acid is used as the phthalic acid or phthalate salt, 0.02 M $Ca^{2+}$ is preferably added to the reaction system for 0.02 M phthalic acid.

In the case that the antigen is a substance having a plurality of binding sites for at least one kind of antibody, the antibody is preferably a monoclonal antibody binding to the plurality of binding sites of the antigen. The monoclonal antibody is produced from a hybridoma cell strain. The hybridoma cell strain is established by separating only one cell from a fused cell group having both antibody production capability and strong growth capability, which are obtained by cell fusion between B cell producing an antibody and myeloma cell, and growing the separated cell. Produced antibodies have the same property. Since the hybridoma cell strain is strong in growth capability and can be preserved in a frozen state, it will never be run out under an appropriate control. Therefore, by culturing the hybridoma cell strain in a medium or in an abdominal cavity and purifying the cultured hybridoma cell strain, the antibodies having the same property can be continuously obtained eternally.

A polyclonal antibody is obtained in the following manner. An antigen is administered to an animal, to allow an antibody binding to the antigen to emerge in the blood in a large amount. The entire or part of the blood is collected and purified. Therefore, the nature of the polyclonal antibody depends on the individuality, growing environment, conditions and the like of the animal. It is therefore difficult to continuously obtain antibodies having the same property.

By use of a monoclonal antibody, antibodies invariably having the same property can be used, and this stabilizes supply of the antibody as the reagent. This results in stabilizing the results of the immunoreaction measurement by the immunoreaction measurement method and the reagent kit for immunoreaction measurement of this embodiment.

The antibody used for the immunoreaction measurement method and the reagent kit for immunoreaction measurement of this embodiment is not specifically limited, but may be of any of classes of IgG, IgM, IgE, IgA and IgD as long as the antibody specifically binds to the antigen. Among others, IgG antibody is preferred for the reasons that IgG antibody is less likely to cause non-specific reaction and that IgG antibody is on the market in a comparatively large number and thus easily available. The animal species from which the antibody is derived is not specifically limited, but antibodies derived from rabbits, goats and mice are preferred because they are comparatively easily available and have been used in many cases.

EXAMPLES

Hereinafter, examples of the present invention will be described. Note that the present invention is not limited to these examples.

Example 1

Hereinafter, construction of a reagent kit for immunoreaction measurement to be used when the subject substance is human albumin will be described. In this example, a method for producing a reagent kit for immunoreaction measurement including an antibody solution and a buffer solution containing phthalic acid or phthalate salt, usable for measurement by slide agglutination, immunonephelometry and immunoturbidimetry, will be described.

Pure water filtered with Milli-Q SP TOC (from Millipore Corp.) was used for preparation of a buffer solution described below. Note that as reagents such as salt and buffering agents, those from Wako Pure Chemical Industries, Ltd. were used unless otherwise specified, and the guaranteed reagent grade was used for polyethylene glycol 5,000 and trans-aconitic acid, while the extra pure grade was used for the others.

First, an antibody solution was prepared. A rabbit anti-human albumin polyclonal antibody was obtained by purifying an antiserum collected from a rabbit immunized against human albumin (from Wako Pure Chemical Industries, Ltd.) by protein A column chromatography. The column was filled with protein A stationary gel from Amersham Pharmacia. An equilibrium buffer solution composed of 1.5 M glycine and 3.0 M NaCl, pH 8.9 was used for purification, and an elution buffer solution composed of 0.1 M citric acid, pH 4.0 was used.

The purification was performed in the following manner. The column was made equilibrium by allowing the equilibrium buffer solution of a volume five times as large as the gel volume filled in the column to flow through the column. The antiserum including the antibody in an amount of 10% to 20% of the entire column binding capacity was diluted double in volume with the equilibrium buffer solution, and the diluted solution was allowed to flow through the column, to enable the antibody in the serum to bind to the protein A. The equilibrium buffer solution was allowed to flow until serum components failing to adsorb to the protein A no more came out from the column, to wash the column. Subsequently, the elution buffer solution was allowed to flow through the column, to elute the antibody binding to the protein A. The eluted antibody fraction was put in a dialysis tube having a fractional molecular weight of 10,000, and dialyzed several times with about a hundred-fold volume of a buffer solution composed of 0.05 M 3-(N-morpholino) propanesulfonic acid (from Dojin, hereinafter, referred to as MOPS), 0.15 M NaCl and 0.04 wt. % $NaN_3$, pH 7.4, for replacement of buffer components. Thereafter, the antibody concentration was estimated by 280 nm absorbance measurement, and adjusted with the same buffer solution as that used for the dialysis to obtain an antibody concentration of 3.0 mg/ml, to thereby obtain the antibody solution. The antibody concentration is not limited to this. The prepared antibody solution may be stored at room temperature, but preferably stored at low temperature, more preferably at 4° C., from the standpoint of prevention of denaturation of the antibody.

A buffer solution containing phthalic acid or phthalate was prepared in the following manner. As the phthalic acid and phthalate salt, phthalic acid and potassium hydrogen phthalate were used, and buffer solutions containing the respective substances were prepared.

The buffer solution containing potassium hydrogen phthalate was prepared in the following manner. Potassium hydrogen phthalate and polyethylene glycol 6,000, measured to have respective final concentrations of 0.05 M and 4 wt. %, were dissolved in pure water of about 90% of the target volume. An aqueous NaOH solution was then added to the resultant solution to adjust the pH to 4.5, and the resultant solution was adjusted with pure water to have the target volume. The prepared buffer solution was stored at room temperature.

The buffer solution containing phthalic acid was prepared in the following manner. Phthalic acid and polyethylene glycol 6,000, measured to have respective final concentrations of 0.03 M and 4 wt. %, were dissolved in pure water of about 90% of the target volume. An aqueous NaOH solution was then added to the resultant solution to adjust the pH to 4.5, and the resultant solution was adjusted with pure water to have the target volume. The prepared buffer solution was stored at room temperature.

At least one of the buffer solutions containing phthalic acid or phthalate salt is combined with the antibody solution, to thereby constitute the reagent kit for immunoreaction measurement.

Example 2

Next, construction of a reagent kit for immunoreaction measurement to be used when the subject substance is human CRP will be described. Human CRP, composed of five subunits having the same structure, is a substance having a plurality of binding sites for one kind of antibody. Therefore, by use of one kind of anti-CRP monoclonal antibody, it is possible to prepare a reagent kit for immunoreaction measurement usable for homogeneous immunoreaction measurement. Two or more kinds of monoclonal antibodies may be used.

In this example, therefore, produced was a reagent kit for immunoreaction measurement including two kinds of antibody solutions including a polyclonal antibody solution and a monoclonal antibody solution and a buffer solution containing phthalic acid or phthalate salt.

First, a method for preparing the polyclonal antibody solution will be described.

A goat antihuman CRP polyclonal antibody was obtained by purifying an antiserum collected from a goat immunized against human CRP by protein G column chromatography. The column was filled with protein G stationary gel from Amersham Pharmacia. An equilibrium buffer solution composed of 0.02 M $Na_2HPO_4$—$NaH_2PO_4$, pH 7.0 was used for purification, and an elution buffer solution composed of 0.1 M glycine, pH 2.7 was used. Purification by column chromatography and replacement of the buffer solution by dialysis were performed in the manner described in Example 1. The antibody concentration was estimated by 280 nm absorbance measurement, and adjusted with the same buffer solution as that used for the dialysis to obtain an antibody concentration of 1.0 mg/ml, to thereby obtain the polyclonal antibody solution.

Human CRP structurally changes depending on whether or not $Ca^{2+}$ is held. Therefore, if an antibody that does not bind to human CRP holding no $Ca^{2+}$ is contained in the antibody solution constituting the reagent kit for immunoreaction measurement, the reaction rate of the antigen-antibody reaction may possibly decrease because human CRP holding no $Ca^{2+}$ increases due to the chelating function of the phthalic acid or phthalate salt. Since the polyclonal antibody solution is prepared in this example, an antibody that does not bind to human CRP holding no $Ca^{2+}$ is included in the polyclonal antibody solution. In view of this, in preparation of the buffer solution containing phthalic acid or phthalate salt described below, $Ca^{2+}$ was added to the buffer solution to maintain the structure of the human CRP.

More specifically, the preparation of the buffer solution containing phthalic acid or phthalate salt was performed in the following manner. In this example, phthalic acid was used as the phthalic acid or phthalate salt.

Phthalic acid, $CaCl_2$ and polyethylene glycol 6,000, measured to have respective final concentrations of 0.02 M, 0.02 M and 4 wt. %, were dissolved in pure water of about 90% of the target volume. An aqueous NaOH solution was then added to the resultant solution to adjust the pH to 4.5, and the resultant solution was adjusted with pure water to have the target volume. The prepared buffer solution was stored at room temperature.

Next, a method for preparing the monoclonal antibody solution will be described.

As the monoclonal antibody, used was an antibody that would not lose the binding capability to human CRP even with addition of a chelating agent (for example, 0.02 M phthalic acid or ethylenediaminetetraacetic acid) to the reaction system, that is, could specifically bind even to human CRP holding no $Ca^{2+}$. Specifically, the monoclonal antibody solution was prepared in the following manner.

A mouse antihuman CRP monoclonal antibody used in this example was obtained as follows. First, hybridoma cells (Accession Number FERM BP-6620 of National Institute of Bioscience and Human Technology) producing a mouse antihuman CRP monoclonal antibody were injected into the abdominal cavity of a mouse and grown to obtain ascites. The resultant ascites was purified by the column chromatography described in Example 1, to obtain the mouse antihuman CRP monoclonal antibody sample.

Concretely, ascites was obtained in the following manner. Retired female BALB/c mice were used for production of ascites. Into the abdominal cavities of the mice, 0.5 to 1 ml of pristane was injected, and after about 7 days, 0.5 to 1 ml of the following cell suspension was injected. Ascites were collected from the mice sequentially in the order in which production of ascites was observed. The hybridoma cell suspension injected into the abdominal cavities was obtained in the following manner. The hybridoma cells were grown by culturing in a medium obtained by mixing 5 to 15 vol. % of a bovine fetus serum in RPMI 1640 medium (from SIGMA), and the grown ones were washed by centrifugation with the RPMI 1640 medium, and re-suspended in the RPMI 1640 medium to provide a concentration of $1 \times 10^6$ to $10^7$ cells/ml.

The mouse antihuman CRP monoclonal antibody sample purified by column chromatography was put in a dialysis tube having a fractional molecular weight of 10,000, and dialyzed several times with a PBS buffer solution containing about a hundred-fold volume of 0.04 wt. % $NaN_3$ (8 g/l NaCl, 0.2 g/l KCl, 1.15 gl $Na_2HPO_4 \cdot 12H_2O$ and 0.2 g/l $KH_2PO_4$, pH 7.4), for replacement of buffer solution components. Subsequently, the antibody concentration was estimated by 280 nm absorbance measurement, and adjusted with the same buffer solution as that used for the dialysis to obtain an antibody concentration of 1.0 mg/ml, to thereby obtain the monoclonal antibody solution.

The buffer solution containing phthalic acid or phthalate salt was prepared in the following manner. Potassium hydrogen phthalate was used as the phthalic acid or phthalate salt to prepare the buffer solution. The antibody of the monoclonal antibody solution in this example is not affected by a change in structure depending on whether or not human CRP holds $Ca^{2+}$. In this case, therefore, there was no addition of $Ca^{2+}$ to the buffer solution.

The buffer solution containing potassium hydrogen phthalate was prepared in the following manner. Potassium hydrogen phthalate and polyethylene glycol 6,000, measured to have respective final concentrations of 0.05 M and 4 wt. %, were dissolved in pure water of about 90% of the target volume. An aqueous NaOH solution was then added to the resultant solution to adjust the pH to 4.5, and the resultant solution was adjusted with pure water to have the target volume. The prepared buffer solution was stored at room temperature.

The concentrations of the antibody solutions prepared as described above are not limited to those described above. The prepared antibody solutions may be stored at room temperature, but are preferably stored at low temperature, more preferably at 4° C., from the standpoint of prevention of denaturation of the antibodies.

The buffer solution containing phthalic acid or phthalate salt prepared as described above is combined with the antibody solution, to constitute the reagent kit for immunoreaction measurement.

The reagents prepared in Examples 1 and 2 are used in the following manner. A sample (analyte) containing an antigen, the antibody solution and the buffer solution containing phthalic acid or phthalate salt are mixed to construct a reaction system. Mixing may be performed in an arbitrary way. The mixing ratio may be determined depending on the measurement range of the antigen concentration required. Antigen-antibody reaction occurs in the reaction system constructed by the mixing, forming agglutinate complexes. The degree of turbidity caused by the agglutinate complexes is estimated by measuring an amount of change in scattered light intensity or the like. The antigen concentration of the analyte can be known based on the estimation results.

By the mixing, the concentrations of the buffering agent, the phthalic acid or phthalate salt and the additives such as polyethylene glycol 6,000 are diluted from the initial concentrations. However, as long as the difference between the diluted concentration and the initial concentration is within about 10%, the measurement results will not be different so large from the measurement results expected from the initial concentration, and thus the dilution will not affect so much. To avoid a concentration change due to the dilution, the antibody solution and the buffer solution containing phthalic acid or phthalate salt may be prepared so that the substances in the reagent will have respective target concentrations during the mixing.

Although not shown in Examples 1 and 2, the antibody may be immobilized on particulate carriers such as latex, gold colloids and magnetic particulates, or may be labeled with an enzyme, a pigment, a fluorescent substance, a luminous substance and the like.

The buffering agent used for preparation of the antibody solution and the pH of the antibody solution are not limited to those described above. For example, in the case of constructing a one-liquid type reagent, phthalic acid or phthalate salt is included in the antibody solution. In this case, the dialysis may be performed with an acidic buffer solution containing phthalic acid or phthalate salt, to maintain the pH of the reaction system at less than 7.

In Examples 1 and 2, NaOH was used for pH adjustment. Alternatively, hydroxides such as KOH, LiOH, $NH_4OH$, $Ca(OH)_2$ and $Mg(OH)_2$ may be used.

In Examples 1, and 2, potassium hydrogen phthalate and phthalic acid were used for preparation of the buffer solution containing phthalic acid or phthalate salt. Alternatively, other kinds of phthalic acid or phthalate salt may be used. For example, any of phthalic anhydride, potassium phthalate, disodium phthalate, ammonium phthalate and copper (II) phthalate may be used. A combination of any of these kinds may also be used. The pH adjustment in this case may be made using HCl and the like when the pH in the state of being dissolved in pure water is more alkaline than the target pH, or using a hydroxide described above and the like when the pH is more acidic than the target pH. The pH adjustment may also be made by adjusting the mixing ratio of the above-exemplified kinds of phthalic acid and phthalate salt.

In the production methods described in Examples 1 and 2, the main buffering capability of the buffer solution containing phthalic acid or phthalate salt was provided by the phthalic acid or phthalate salt. However, the concentration of the phthalic acid or phthalate salt added to the buffer solution is not specifically limited. Also, the main buffering capability of the buffer solution containing phthalic acid or phthalate salt may be provided by another buffering agent, or the buffering capability may be provided through coordination between the phthalic acid or phthalate salt and another buffering agent.

Example 3

In this example, the effect of the antigen measurement in the acidic reaction system containing phthalic acid or phthalate salt according to the present invention is described in comparison with antigen measurement in a neutral reaction system generally used in immunoreaction measurement methods. The comparison was made by measuring human albumin by immunonephelometry. As the reagent for constituting the acidic reaction system containing phthalic acid or phthalate salt, the one constructed in Example 1 was used.

Hereinafter, the buffer solutions using potassium hydrogen phthalate and using phthalic acid prepared in Example 1 are respectively called the potassium hydrogen phthalate buffer solution and the phthalic acid buffer solution.

As comparative examples, MOPS was used for buffer solutions for constituting neutral reaction systems. Specifically, buffer solutions having a composition of 0.05 M MOPS and 4 wt. % polyethylene glycol 6,000, pH 7.4 and a composition of 0.03 M MOPS and 4 wt. % polyethylene glycol 6,000, pH 7.4 were prepared. Hereinafter, these buffer solutions are respectively called the 0.05 M MOPS buffer solution and the 0.03 M MOPS buffer solution. The buffer solutions were stored at room temperature.

Human albumin solutions having human albumin concentrations of 0, 5, 10, 20, 30, 50, 70, 100, 200, 300 and 500 mg/dl were prepared using human albumin (from Wako Pure Chemical Industries, Ltd.) as the antigen and a buffer solution having a composition of 0.05 M MOPS and 0.4 wt. % $NaN_3$, pH 7.4. The human albumin solutions were stored at 4° C. until they were used.

For the measurement, a spectrofluorometer (from Shimadzu Corporation, Model RF-5300PC) was used. A constant temperature cell holder (from Shimadzu Corporation, Model 206-15440) connected to a constant temperature water bath (from TAITEC, product name: COOLNIT BATH EL-15) was placed in a sample chamber of the spectrofluorometer. Water kept at 25° C. was allowed to circulate in the water bath, so that the temperature in the quartz cell could be kept constant during the measurement. The measurement conditions of the spectrofluorometer were as follows: both the excitation and emission wavelengths were set at 670 nm, the bandwidth was set at 3 nm on both the emission/ excitation sides, and the sensitivity was set at high.

The measurement was performed in the following manner. The antibody solution prepared in Example 1, 0.1 ml, was added to each 2.87 ml of the buffer solutions and stirred. To the resultant mixed solutions, each 0.03 ml of the human albumin solutions having the above concentrations were added and stirred. Therefore, the concentration of the rabbit antihuman albumin polyclonal antibody in the reaction system will be about 0.10 mg/ml, and the concentration of the human albumin will be a value obtained by multiplying the concentration of the human albumin solution used for the measurement by 0.01. Each of the resultant mixture was put in the quartz cell for fluorescence analysis, which was placed in the spectrofluorometer. A T-shape thermocouple (from RS Components, Model 219-4696) was immersed in the quartz cell. Time course measurement was performed from the time point 2 minutes after the mixing of the human albumin at intervals of 0.04 seconds for 300 seconds. The temperature in the quartz cell during the measurement was monitored by connecting the T-shape thermocouple to a digital multi-thermometer (from Advantest, Model TR2114). To prevent influence of contamination of the quartz cell on the measurement, correction was made with a value measured by putting pure water in the cell before measurement of each reaction. An average of measured values obtained during 200 to 300 seconds was computed, and the resultant average was determined as the measured value for the human albumin solution having each concentration. After the measurement, the pH of each reaction system mixed solution was measured with a pH meter to examine influence of the mixing of each buffer solution, the antibody solution and the human albumin solution having each concentration on the pH of the reaction system.

The results of the measurement are as follows. The pH of the reaction system mixed solution composed of each buffer solution, the antibody solution and the human albumin solution having each concentration was roughly the same as the pH of the buffer solution. The temperature in the cell during the measurement, measured with the thermocouple, remained at 25.5±1° C.

Figure 4:
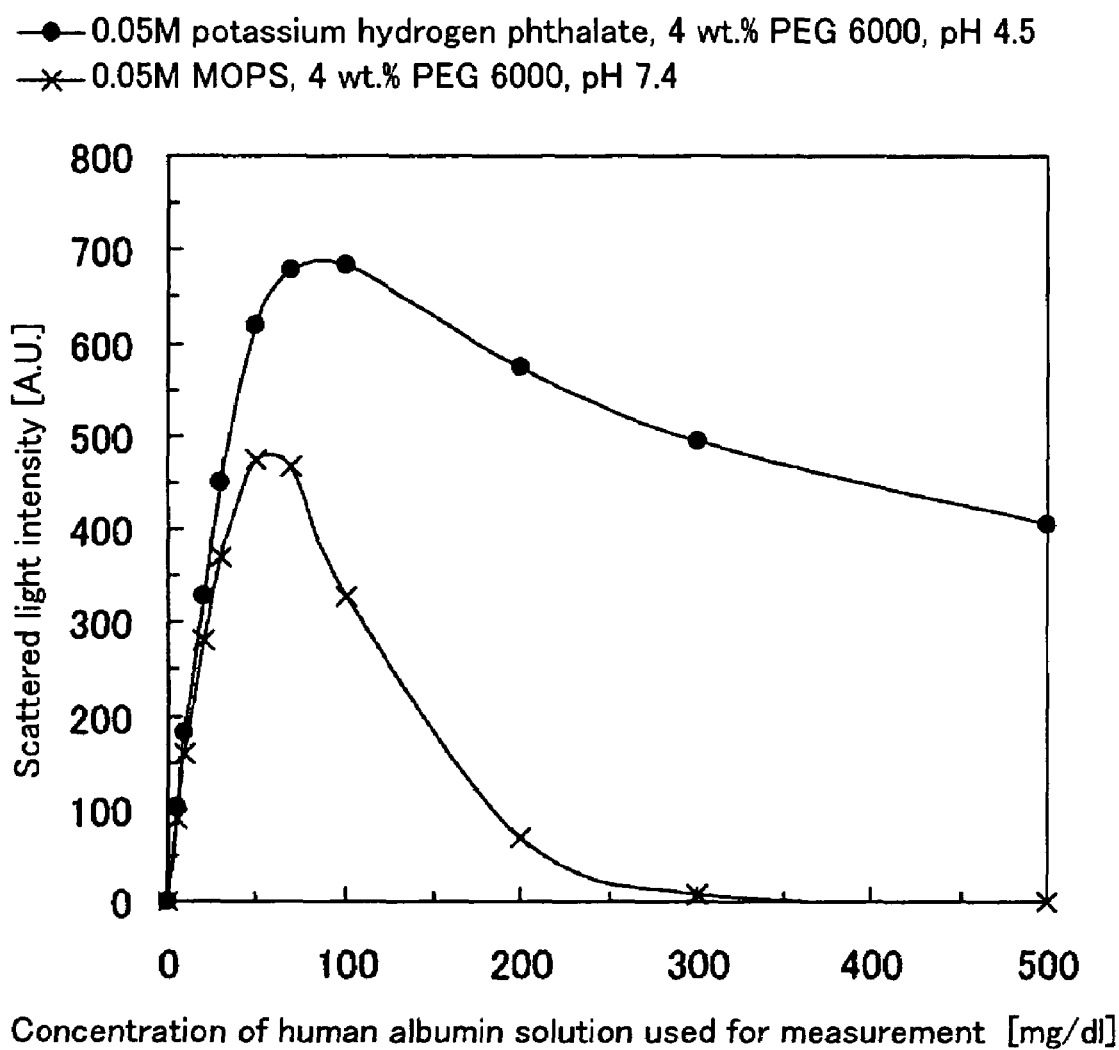
FIG. 4 is a graph showing the results of human albumin measurement by immunonephelometry, in an immunoreaction measurement method using a reagent kit for immunoreaction measurement including potassium hydrogen phthalate of an example of the present invention and in a comparative example.

FIG. 4 is a view obtained by plotting the results of the measurement performed after the addition of the human albumin solutions having the concentrations up to 500 mg/dl to the reaction system including the 0.05 M potassium hydrogen phthalate buffer solution and the reaction system including the 0.05 M MOPS buffer solution. The Y-axis represents the scattering light intensity and the X-axis represents the concentration of the human albumin solution used for the measurement. A higher scattering light intensity indicates a higher degree of turbidity of the reaction system and formation of a large amount of agglutinate complexes. Each of the plotted values is a value obtained by subtracting the value measured when the human albumin concentration is 0 mg/dl from the measured value for the human albumin solution having each concentration.

As shown in FIG. 4, evidently higher measured values were exhibited when the 0.05 M potassium hydrogen phthalate buffer solution was used for the measurement than when the 0.05 M MOPS buffer solution was used. Also, when the 0.05 M MOPS buffer solution was used, the measured value peaked near 50 mg/dl and greatly decreased with increase of the concentration of the human albumin due to the zone phenomenon. However, when the 0.05 M potassium hydrogen phthalate buffer solution was used, the measured value peaked near 70 to 100 mg/dl and was suppressed from decreasing with increase of the concentration of the human albumin due to the zone phenomenon.

Figure 5:
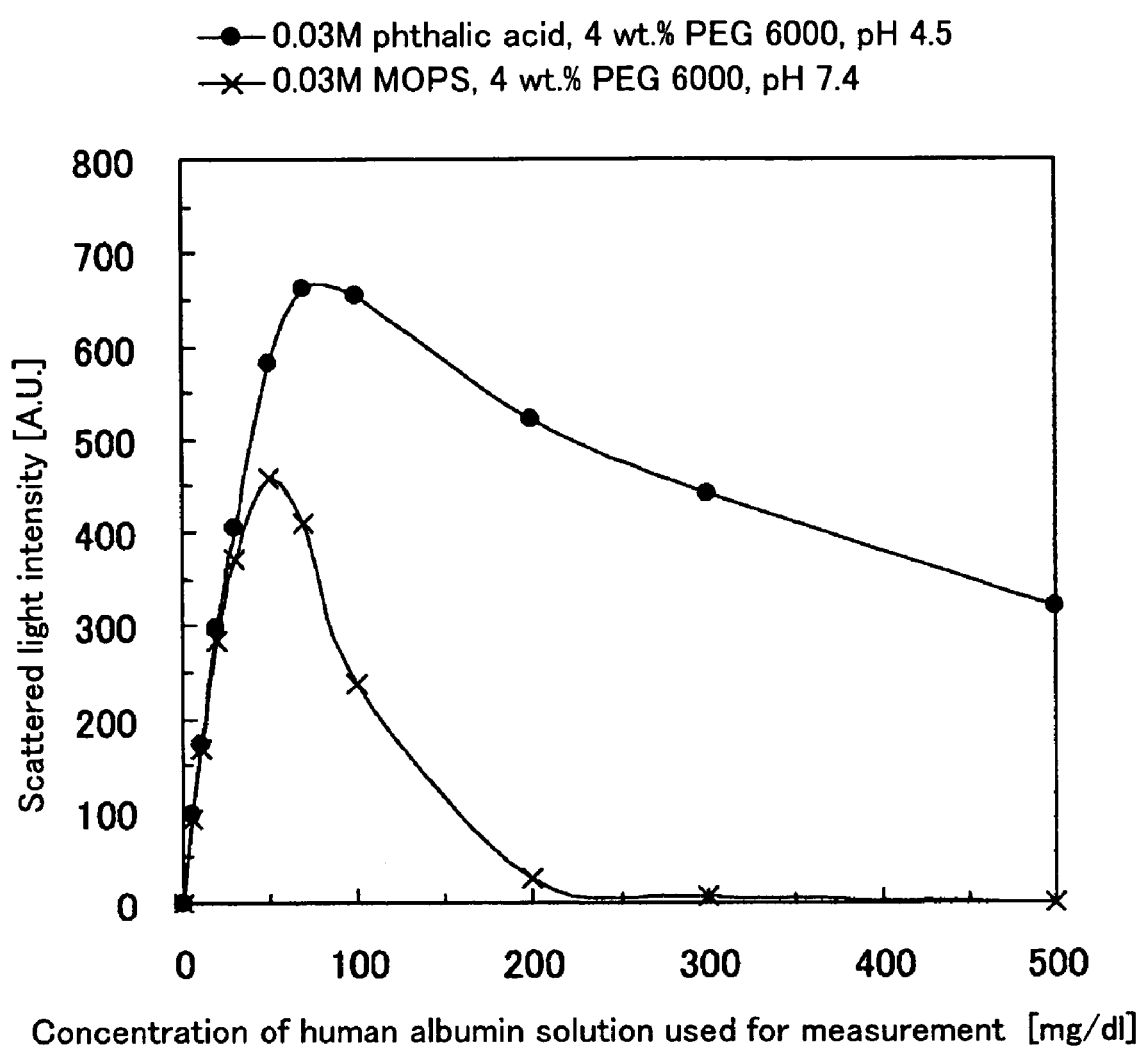
FIG. 5 is a graph showing the results of human albumin measurement by immunonephelometry, in an immunoreaction measurement method using a reagent kit for immunoreaction measurement including phthalic acid of the example of the present invention and in a comparative example.

FIG. 5 is a view obtained by plotting the results of the measurement performed after the addition of the human albumin solutions having the concentrations up to 500 mg/dl to the reaction system including the 0.03 M phthalic acid buffer solution and the reaction system including the 0.03 M MOPS buffer solution. The Y-axis represents the scattering light intensity and the X-axis represents the concentration of the human albumin solution used for the measurement. Each of the plotted values is a value obtained by subtracting the value measured when the human albumin concentration is 0 mg/dl from the measured value for the human albumin solution having each concentration.

As shown in FIG. 5, evidently higher measured values were exhibited when the 0.03 M phthalic acid buffer solution was used for measurement of antigen-antibody reaction than when the 0.03 M MOPS buffer solution was used. Also, when the 0.03 M MOPS buffer solution was used, the measured value peaked near 50 mg/dl and greatly decreased with increase of the concentration of the human albumin due to the zone phenomenon. However, when the 0.03 M phthalic acid buffer solution was used, the measured value peaked near 70 to 100 mg/dl and was suppressed from decreasing with increase of the concentration of the human albumin due to the zone phenomenon.

As is found from the results described above, it was confirmed that the immunoreaction measurement method and the reagent kit for immunoreaction measurement of the present invention could provide a higher measured value than the conventional immunoreaction measurement method and reagent kit for immunoreaction measurement. It was also confirmed that the zone phenomenon could be eased compared with the case of the conventional immunoreaction measurement method and reagent kit for immunoreaction measurement.

In clinical tests, a trace amount of human albumin egested in urine is an object to be measured as an early diagnosis marker of diabetic nephropathy. In many immunoreaction measurement methods and reagent kits for immunoreaction measurement, the range of 0.1 to 20 mg/dl is set as the quantitative range (see New Diabetic Nephropathy—For Protection of Crisis and Prevention of Progress, ed. by Yukio Shigeta and Kazo Kaizu, p. 131 (1992)). In the conventional measurement method by immunonephelometry and the reagent kit used for the method, to ease the zone phenomenon, it is necessary to increase the antibody concentration in the neutral buffer solution constructed as the reaction system, or decrease the antigen concentration by dilution of the neutral buffer solution or other means, utilizing the fact that homogeneous immunoreaction is equilibrium reaction.

However, by adopting the immunoreaction measurement method and the reagent kit for immunoreaction measurement according to the present invention, the zone phenomenon can be eased even when the antibody concentration is low and the antigen concentration is high. Therefore, to discuss based on the measurement results in this example, for example, it is possible to have a wide measurement range up to 500 mg/dl for the reaction system constructed of the 0.05 M potassium hydrogen phthalate buffer solution or the reaction system constructed of the 0.03 M phthalic acid buffer solution, by providing an evaluation region regarding measured values equal to or more than that for 20 mg/dl as positive values. In the neutral buffer solution system in the comparative example, however, the measurement range is limited to up to about 120 to 130 mg/dl.

As described above, in the immunoreaction measurement method and the reagent kit for immunoreaction measurement according to the present invention, human albumin in a wider concentration range, compared with the case of measurement in the conventional neutral buffer solution system, can be measured without the necessity of considering the influence of the zone phenomenon.

Example 4

The pH dependence of the measured value obtained by the immunoreaction measurement method and the reagent kit for immunoreaction measurement according to the present invention, using potassium hydrogen phthalate as the phthalic acid or phthalate salt, was examined by immunonephelometry. Details of this examination are as follow. Human albumin was used as the subject substance. Human albumin solutions were prepared in the manner described in Example 3, to have concentrations of 0, 5, 10, 20, 30, 50, 70, 100, 200, 300 and 500 mg/dl. The antibody solution used in Example 1 was also used in this example.

As the buffer solution constituting the reaction system for examining the pH dependence of the measured value, prepared were 0.05 M potassium hydrogen phthalate buffer solutions containing 0.05 M potassium hydrogen phthalate and 4 wt. % polyethylene glycol 6,000, with pH's adjusted to 4.0, 4.5, 5.0, 5.5 and 6.0.

As the comparative example, a 0.05 M MOPS buffer solution containing 0.05 M MOPS and 4 wt. % polyethylene glycol 6,000 having a pH adjusted to 7.4 was used. The apparatus and the measurement method used in Example 3 were also used in this example.

The results are as follows. The pH of the reaction system mixed solution used for each measurement, composed of each buffer solution, the antibody solution and the human albumin solution having each concentration, was the same as the pH of the buffer solution. The temperature in the quartz cell during the measurement remained at 25.5±1° C.

Figure 6:
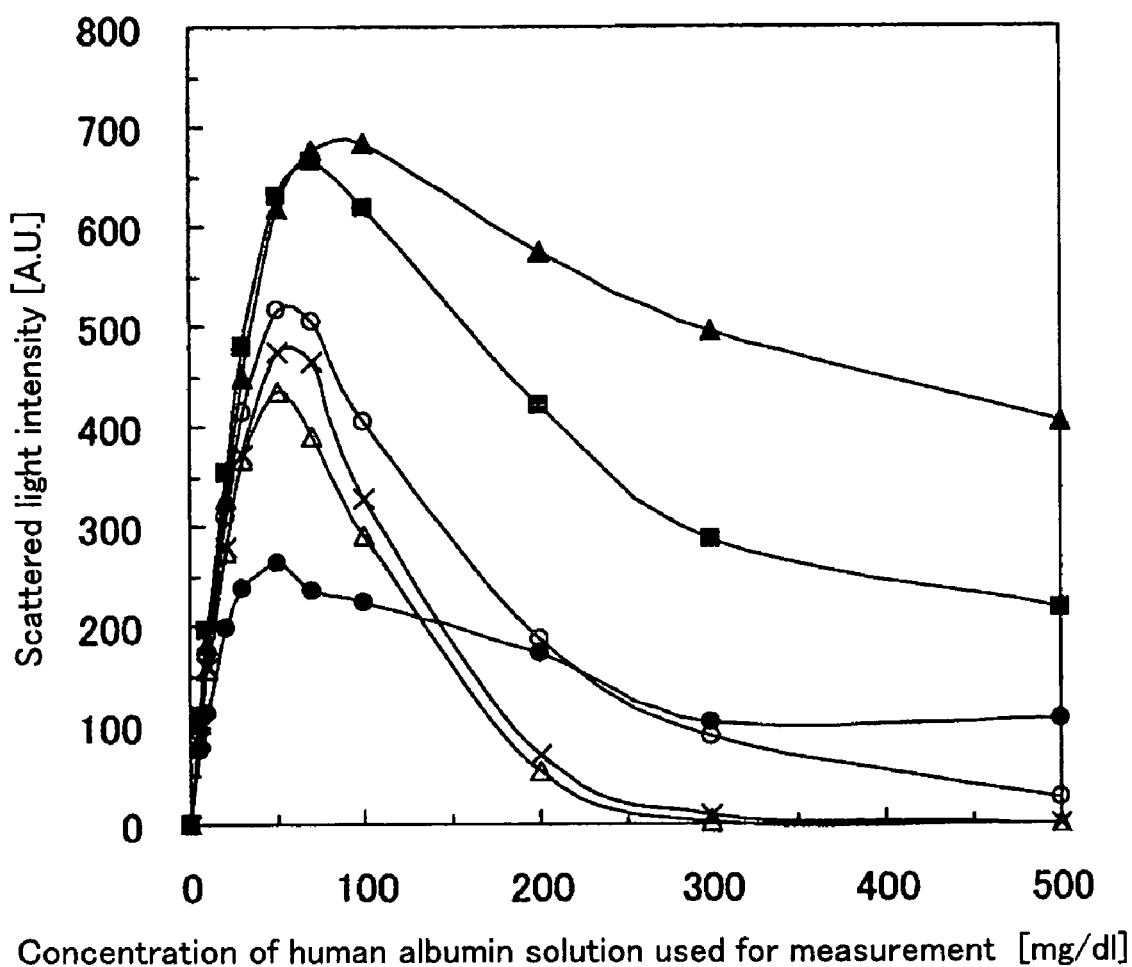
FIG. 6 is a graph showing the results of pH dependence of the human albumin measurement by immunonephelometry, in an immunoreaction measurement method using a reagent kit for immunoreaction measurement including potassium hydrogen phthalate of another example of the present invention.

The results are shown in FIG. 6. FIG. 6 is a view obtained by plotting the results of the measurement performed after the addition of the human albumin solutions having the concentrations up to 500 mg/dl to the reaction systems constructed of the 0.05 M potassium hydrogen phthalate buffer solutions having the respective pH's. The Y-axis represents the scattering light intensity and the X-axis represents the concentration of the human albumin solution used for the measurement. Each of the plotted values is a value obtained by subtracting the value measured when the human albumin concentration is 0 mg/dl from the measured value for the human albumin solution having each concentration. The reading of the graph is the same as that in FIG. 4.

When the measurement was performed using the reaction systems constructed of the 0.05 M potassium hydrogen phthalate buffer solutions having pH's in the range of 4.5 to 5.5, the measured values were higher than those obtained by the measurement using the reaction system constructed of the 0.05 M MOPS buffer solution as the comparative example. In addition, the effect of easing the zone phenomenon occurring with increase of the antigen concentration was exhibited. This effect was greatest for the reaction system constructed of the 0.05 M potassium hydrogen phthalate buffer solution having a pH of 4.5. From the results in FIG. 6, it was considered that the effects of improving the measured value and easing the zone phenomenon could be obtained significantly stably by using the reaction system constructed of the 0.05 M potassium hydrogen phthalate buffer solution having a pH of 4.5 to 5.3, preferably a pH of 4.5 to 5.0.

When the reaction system was constructed of the 0.05 M potassium hydrogen phthalate buffer solution having a pH of 6.0, the measured values were lower than those obtained by the measurement using the reaction system constructed of the 0.05 M MOPS buffer solution. In this case, the measured value curve was similar in shape to that obtained when the reaction system was constructed of the 0.05 M MOPS buffer solution, failing to exhibit the effect of easing the zone phenomenon occurring with increase of the antigen concentration.

When the reaction system was constructed of the 0.05 M potassium hydrogen phthalate buffer solution having a pH of 4.0, the measured values were lower than those obtained by the measurement using the reaction system constructed of the 0.05 M MOPS buffer solution in the case of adding up to 100 mg/dl of human albumin to the reaction system. However, in the case of adding 200 mg/dl or more of human albumin to the reaction system, the measured values were higher than those obtained by the measurement using the reaction system constructed of the 0.05 M MOPS buffer solution, exhibiting the effect of easing the zone phenomenon occurring with increase of the antigen concentration.

From the results described above, it was found that in the immunoreaction measurement method using phthalic acid or phthalate salt, the pH of the reaction system should preferably be set at 4.5 to 5.5, more preferably at 4.5 to 5.3, further more preferably at 4.5 to 5.0. Also found was that the greatest effect was obtained by setting the pH of the reaction system at 4.5.

Likewise, it was found that the reagent kit for immunoreaction measurement using phthalic acid or phthalate salt should preferably be prepared so that the pH of the reaction system be set at 4.5 to 5.5, more preferably at 4.5 to 5.3, further more preferably at 4.5 to 5.0. Also found was that the greatest effect was obtained by preparing the reagent kit so that the pH of the reaction system be set at 4.5.

Example 5

The dependence of the measured value obtained by the immunoreaction measurement method and the reagent kit for immunoreaction measurement according to the present invention, using potassium hydrogen phthalate as the phthalic acid or phthalate salt, on the concentration of the phthalic acid or phthalate salt was examined by immunonephelometry. Details of this examination are as follow. Human albumin was used as the subject substance. Human albumin solutions were prepared in the manner described in Example 3, to have concentrations of 0, 5, 10, 20, 30, 50, 70, 100, 200, 300 and 500 mg/dl. The antibody solution used in Example 1 was also used in this example.

As the buffer solution constituting the reaction system for examining the dependence of the measured value on the concentration of the phthalic acid or phthalate salt, prepared were potassium hydrogen phthalate buffer solutions having concentrations of potassium hydrogen phthalate of 0.01, 0.025, 0.05, 0.1, 0.2 and 0.3 M including 4 wt. % polyethylene glycol 6,000, pH 4.5.

As the comparative example, a 0.05 M MOPS buffer solution including 0.05 M MOPS and 4 wt. % polyethylene glycol 6,000 having a pH adjusted to 7.4 was used. The apparatus and the measurement method used in Example 3 were also used in this example.

The results are as follows. The pH of the mixed solution used for each measurement, composed of each buffer solution, the antibody solution and the human albumin solution having each concentration, was 4.7 when the 0.01 M potassium hydrogen phthalate buffer solution was used, 4.6 when the 0.025 M potassium hydrogen phthalate buffer solution was used, and 4.5 when the other potassium hydrogen phthalate buffer solutions were used. The temperature in the quartz cell during the measurement remained at 25.5±1° C.

Figure 7:
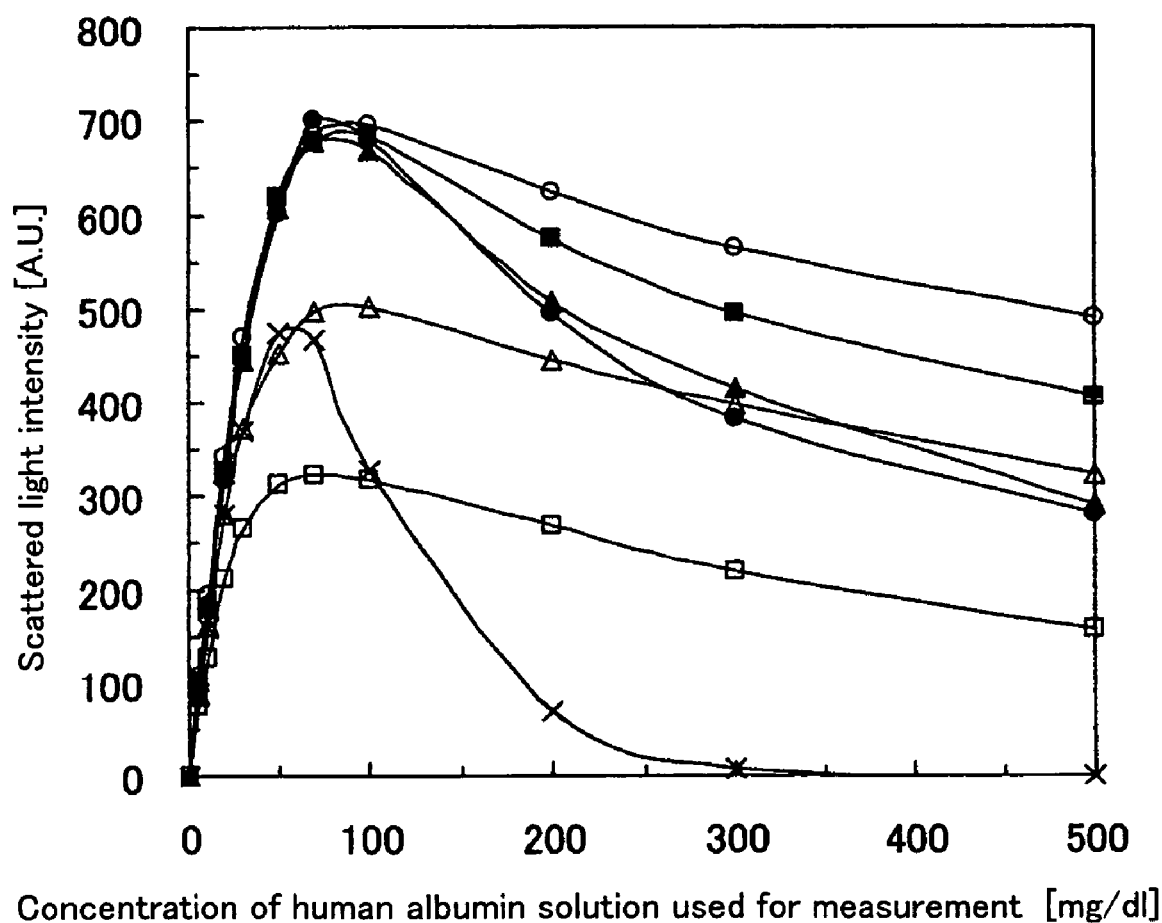
FIG. 7 is a graph showing the results of dependence of the human albumin measurement by immunonephelometry on the concentration of potassium hydrogen phthalate, in an immunoreaction measurement method using a reagent kit for immunoreaction measurement including potassium hydrogen phthalate of yet another example of the present invention.

The results are shown in FIG. 7. FIG. 7 is a view obtained by plotting the results of the measurement performed after the addition of the human albumin solutions having the concentrations up to 500 mg/dl to the reaction systems constructed of the potassium hydrogen phthalate buffer solutions having the respective concentrations and a pH of about 4.5. The Y-axis represents the scattering light intensity and the X-axis represents the concentration of the human albumin solution used for the measurement. Each of the plotted values is a value obtained by subtracting the value measured when the human albumin concentration is 0 mg/dl from the measured value for the human albumin solution having each concentration. The reading of the graph is the same as that in FIG. 4.

In the case of the reaction systems constructed of the potassium hydrogen phthalate buffer solutions having concentrations of potassium hydrogen phthalate of 0.2 M or less, the measured values were higher than those obtained from the reaction system constructed of the 0.05 M MOPS buffer solution as the comparative example, confirming the effect of improving the measured value. In addition, the effect of easing the zone phenomenon occurring with increase of the antigen concentration was exhibited. The effect of easing the zone phenomenon was especially high when the reaction system was constructed of any of the potassium hydrogen phthalate buffer solutions having concentrations of 0.1 M or less. While not so large difference was recognized in the effect of improving the measured value among the reaction systems constructed of the potassium hydrogen phthalate buffer solutions having concentrations of 0.1 M or less, the effect of easing the zone phenomenon was highest when the reaction system was constructed of the 0.1 M potassium hydrogen phthalate buffer solution.

When the reaction system was constructed of the 0.3 M potassium hydrogen phthalate buffer solution, the measured values were lower than those obtained when the reaction system was constructed of the 0.05 M MOPS buffer solution as the comparative example, in the case of the human albumin concentrations up to 100 mg/dl. However, in the case of the human albumin concentrations of 200 mg/dl or more, the measured values were higher than those in the comparative example, exhibiting the effect of easing the zone phenomenon occurring with increase of the antigen concentration.

From the results described above, it was found that in the immunoreaction measurement method using phthalic acid or phthalate salt according to the present invention, the concentration of potassium hydrogen phthalate should suitably be set at 0.2 M or less to obtain an effect higher than that obtained from the general neutral buffer solution. In particular, it was found that the concentration of potassium hydrogen phthalate should more preferably be set at 0.1 M or less, most preferably at 0.1 M.

Likewise, it was found that the reagent kit for immunoreaction measurement using phthalic acid or phthalate salt according to the present invention should preferably be prepared so that the concentration of potassium hydrogen phthalate be set at 0.2 M or less. In particular, it was found that the reagent kit should more preferably be prepared so that the concentration of potassium hydrogen phthalate be set at 0.1 M or less, most preferably be prepared so that the concentration of potassium hydrogen phthalate be set at 0.1 M.

Example 6

The measured value obtained by the immunoreaction measurement method and the reagent kit for immunoreaction measurement according to the present invention, using the phthalic acid or phthalate salt together with another buffering agent, was examined by immunonephelometry. Details of this examination are as follow.

Human albumin was used as the subject substance. Human albumin solutions were prepared in the manner described in Example 3, to have concentrations of 0, 5, 10, 20, 30, 50, 70, 100, 200, 300 and 500 mg/dl. The antibody solution used in Example 1 was also used in this example.

Phthalic acid was used as the phthalic acid or phthalate salt, and succinic acid was used as the buffering agent coexisting with the phthalic acid, to constitute a succinic acid/phthalic acid mixed buffer solution containing 0.1 M succinic acid, 0.02 M phthalic acid and 4 wt. % polyethylene glycol 6,000, pH 4.5. As the comparative example having no phthalic acid or phthalate salt, prepared was a succinic acid buffer solution containing 0.12 M succinic acid and 4 wt. % polyethylene glycol 6,000, pH 4.5.

The results are as follows. The pH of the mixed solution used for each measurement, composed of each buffer solution, the antibody solution and the human albumin solution having each concentration, was roughly the same as the pH of the buffer solution. The temperature in the quartz cell during the measurement remained at 25.5±1° C.

Figure 8:
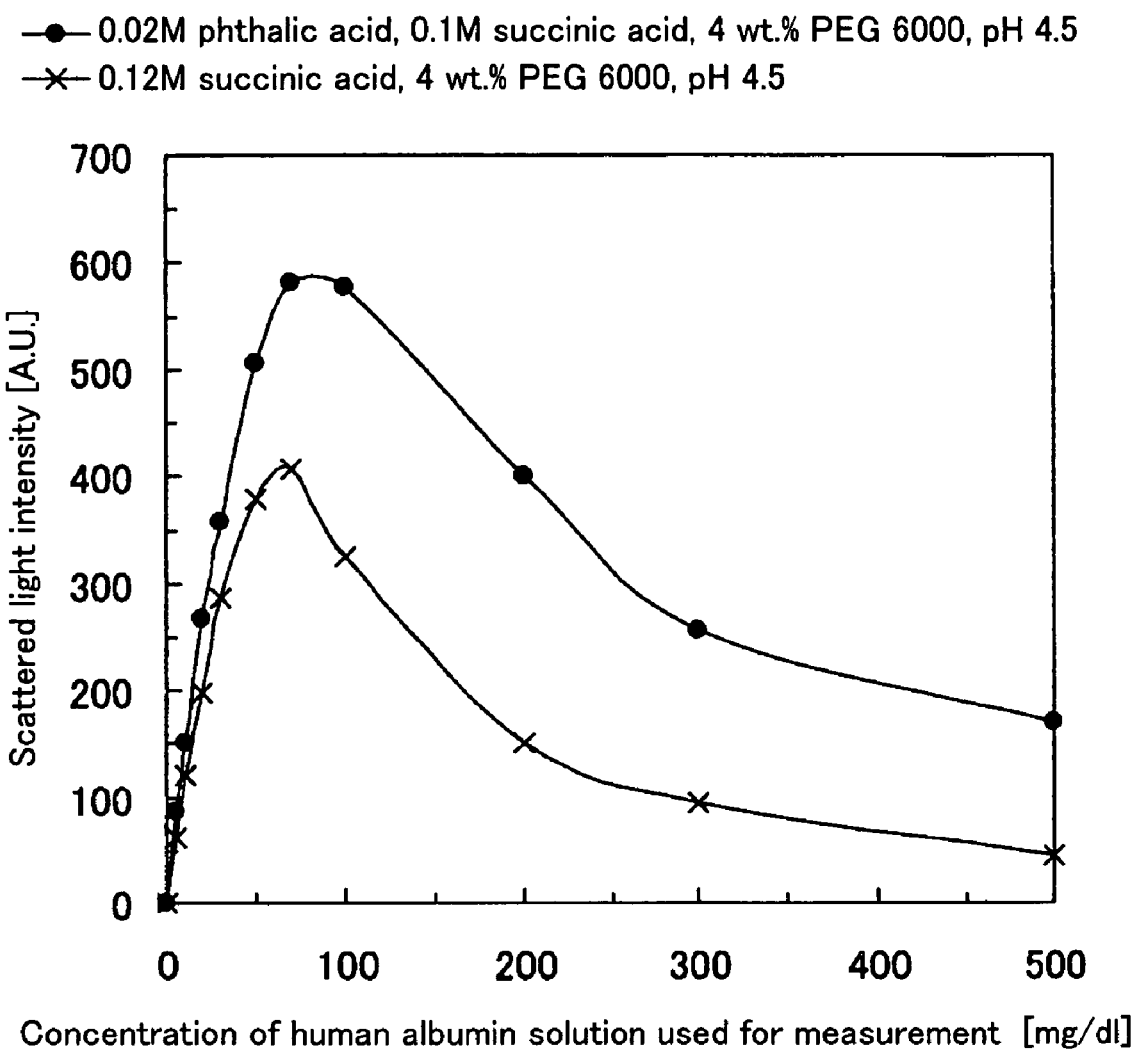
FIG. 8 is a graph showing the results of human albumin measurement by immunonephelometry, in an immunoreaction measurement method using a reagent kit for immunoreaction measurement including phthalic acid and another buffering agent of yet another example of the present invention and in a comparative example.

The results are shown in FIG. 8. FIG. 8 is a view obtained by plotting the results of the measurement performed after the addition of the human albumin solutions having the concentrations up to 500 mg/dl to the respective reaction systems constructed of the succinic acid/phthalic acid mixed buffer solution and the succinic acid buffer solution. The Y-axis represents the scattering light intensity and the X-axis represents the concentration of the human albumin solution used for the measurement. Each of the plotted values is a value obtained by subtracting the value measured when the human albumin concentration is 0 mg/dl from the measured value for the human albumin solution having each concentration. The reading of the graph is the same as that in FIG. 4.

As a result, the measured values improved when the succinic acid/phthalic acid mixed buffer solution was used, compared with the comparative example using the succinic acid buffer solution. The effect was therefore confirmed. In addition, the effect of easing the zone phenomenon occurring with increase of the antigen concentration was exhibited.

From the results described above, it was confirmed that in the immunoreaction measurement method and the reagent kit for immunoreaction measurement according to the present invention, the effect of improving the measured value and the effect of easing the zone phenomenon could be obtained even when the phthalic acid or phthalate salt was used together with another buffering agent.

Example 7

Using the goat antihuman CRP polyclonal antibody solution prepared in Example 2, the effect of the human CRP measurement according to the present invention was examined by comparing with human CRP measurement using a neutral reaction system generally used in the conventional immunoreaction measurement method. The results are described as follows.

Human CRP solutions having respective concentrations used for the measurement were prepared by diluting purified human CRP (from Chemicon International, Lot No. 21042246) with a buffer solution composed of 0.05 M POPS and 0.04 wt. % $NaN_3$, pH 7.4. The concentrations of the human CRP solutions were 0, 10, 20, 30, 50, 70, 100 and 200 mg/dl.

As the antibody solution, the goat antihuman CRP polyclonal antibody solution prepared in Example 2 was used.

As the buffer solution containing phthalic acid or phthalate salt, the phthalic acid buffer solution (0.02 M phthalic acid, 0.02 M $CaCl_2$ and 4 wt. % polyethylene glycol 6,000, pH 4.5) prepared in Example 2 was used.

As the comparative example having no phthalic acid or phthalate salt, a 0.05 M MOPS buffer solution containing 0.05 M MOPS and 4 wt. % polyethylene glycol 6,000 having a pH adjusted to 7.4 was used.

A self-made measurement apparatus as follows was used. A semiconductor laser pointer modulated at 270 Hz, wavelength: 680 nm, output power: 15 mW (from Kikoh Giken, model MLXS-D-12-680-35) was used as the light source. A silicon photo diode for visible to infrared precision photometry (from Hamamatsu Photonics, model S2387-66R) was used as the detector. As the cell, 0.1 cm thick optical glass plates were put together to have a square pole having a capacity of about 200 µl. The cell was placed at a position apart from the light source by 0.5 cm so that one face of the cell is vertical to the light source. The detector was placed at a position forming an angle of 90° with the light source and apart from the cell by 5.5 cm. A shading cylinder was provided between the detector and the cell to avoid stray light from being incident on the detector. The arrangement was made so that a current signal corresponding to the light amount detected by the detector be amplified to a 100× voltage signal via an amplification circuit including a current-voltage converter ($10^6$ V/A) and an operation amplifier, and then subjected to phase-sensitive detection via a lock-in amplifier (from NF Corporation, model 5610B), to enable capturing into a computer under GPIB control.

The measurement of the human CRP having the respective concentrations was performed in the following manner for each buffer solution. Each reaction system was prepared at a mixing ratio of 178 µl of the buffer solution, 9 µl of the human CRP solution and 7 µl of the antibody solution. Therefore, the final concentration of the goat antihuman CRP polyclonal antibody in the reaction system will be about 0.036 mg/ml, and the final concentration of the human CRP will be a value obtained by multiplying the concentration of the human CRP solution used for the measurement by 0.046.

First, the buffer solution and the human CRP solution were mixed by stirring in the cell. Subsequently, the antibody solution of the above volume was added to the mixed solution and stirred, to cause antigen-antibody reaction. Measurement of scattered light was started 10 seconds before the addition of the antibody solution and performed at intervals of 0.5 seconds for 300 seconds. The measured values were obtained as voltage values. To prevent influence of contamination of the cell on the measurement, correction was made with a value measured by putting pure water in the cell before measurement of each reaction. An average of measured values obtained during 200 to 300 seconds was computed, and the resultant average was determined as the measured value for the human CRP solution having each concentration. When occurrence of self-agglutination of the antigen was recognized from the measured values obtained for 10 seconds preceding the addition of the antibody solution, the average of these measured values was subtracted from the above measured value for the human CRP solution having each concentration. The measurement was performed at room temperature (about 20° C.).

Figure 9:
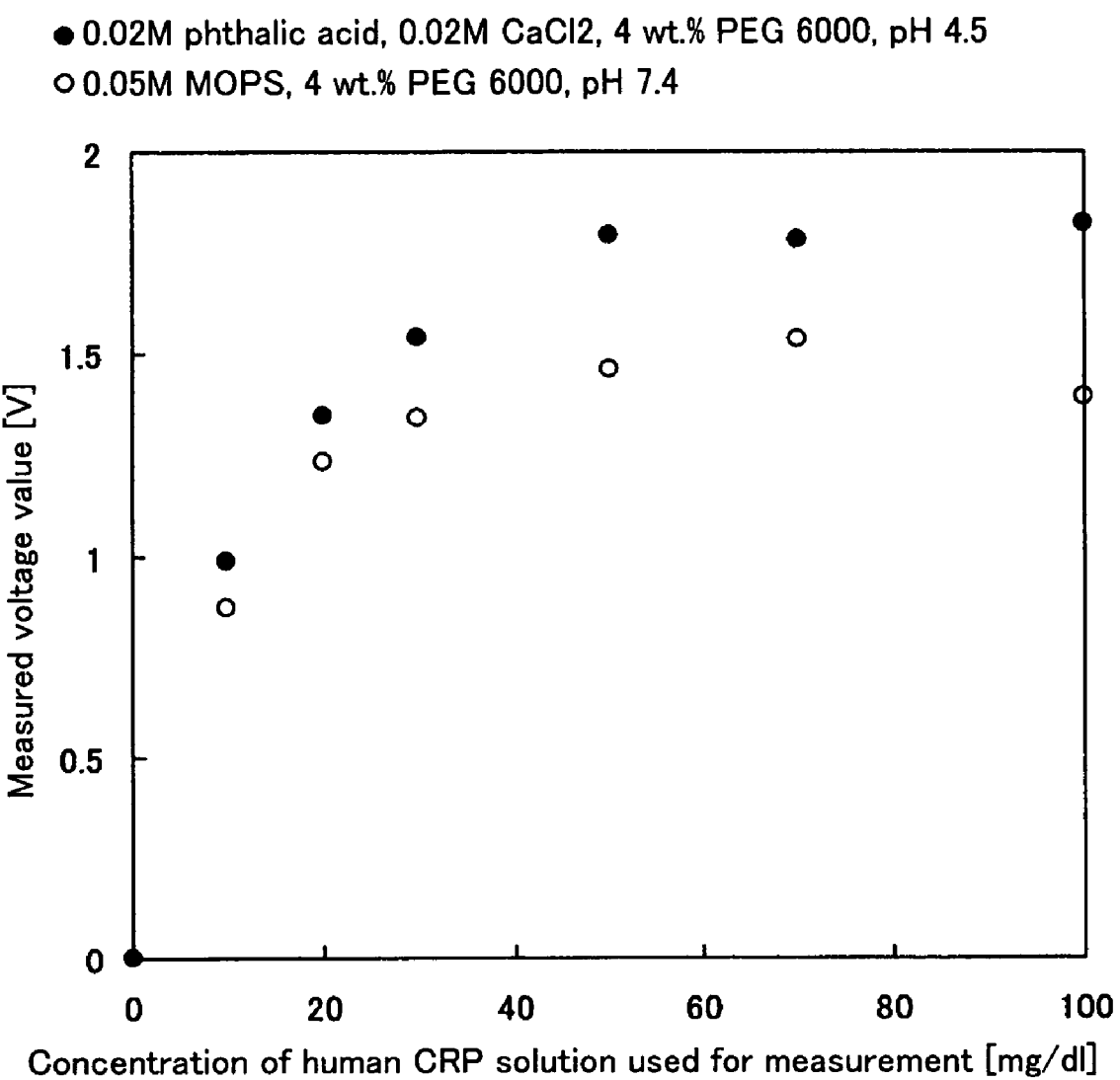
FIG. 9 is a graph showing the results of human CRP measurement by immunonephelometry, in an immunoreaction measurement method using a reagent kit for immunoreaction measurement including a goat antihuman CRP polyclonal antibody and phthalic acid of yet another example of the present invention and in a comparative example.

The results are as follows. FIG. 9 is a view obtained by plotting the results of the measurement performed after the addition of the human CRP solutions having concentrations up to 100 mg/dl to the respective buffer solutions. The Y-axis represents the measured voltage value and the X-axis represents the concentration of the human CRP solution used for the measurement. A higher measured voltage value indicates a larger amount of scattered light incident on the detector, and this indicates that the turbidity of the reaction system is higher, that is, a larger number of agglutinate complexes were formed by the antigen-antibody reaction. Each of the plotted values is a value obtained by subtracting the value measured when the human CRP concentration is 0 mg/dl from the measured value for the human CRP solution having each concentration.

As is found from FIG. 9, it was confirmed that higher measured values were exhibited in the measurement of the human CRP solutions having the respective concentrations in the case of using the reagent kit including the goat antihuman CRP polyclonal antibody solution and the buffer solution containing 0.02 M $CaCl_2$ and phthalic acid, both prepared in Example 2, compared with the case of using the MOPS buffer solution as the comparative example.

Example 8

Using the mouse antihuman CRP monoclonal antibody solution prepared in Example 2, the effect of the human CRP measurement according to the present invention was examined by comparing with human CRP measurement using a neutral reaction system generally used in the conventional immunoreaction measurement method. The results are described as follows.

Human CRP solutions used for the measurement were prepared in the manner described in Example 7, to have concentrations of 0, 10, 20, 30, 50, 70 and 100 mg/dl.

As the antibody solution, the mouse antihuman CRP monoclonal antibody solution prepared in Example 2 was used.

As the buffer solution containing phthalic acid or phthalate salt, the potassium hydrogen phthalate buffer solution (0.05 M potassium hydrogen phthalate and 4 wt. % polyethylene glycol 6,000, pH 4.5) prepared in Example 2 was used.

As the comparative example having no phthalic acid or phthalate salt, a 0.05 M MOPS buffer solution containing 0.05 M MOPS and 4 wt. % polyethylene glycol 6,000 having a pH adjusted to 7.4 was used.

For the measurement, the apparatus having the same construction and the same measurement conditions as those described in Example 7 were used. Also, the measurement method, the method for processing measured data and the like described in Example 7 were used in this example. Therefore, the final concentration of the mouse antihuman CRP monoclonal antibody in the reaction system will be about 0.036 mg/ml, and the final concentration of the human CRP will be a value obtained by multiplying the concentration of the human CRP solution used for the measurement by 0.046.

Figure 10:
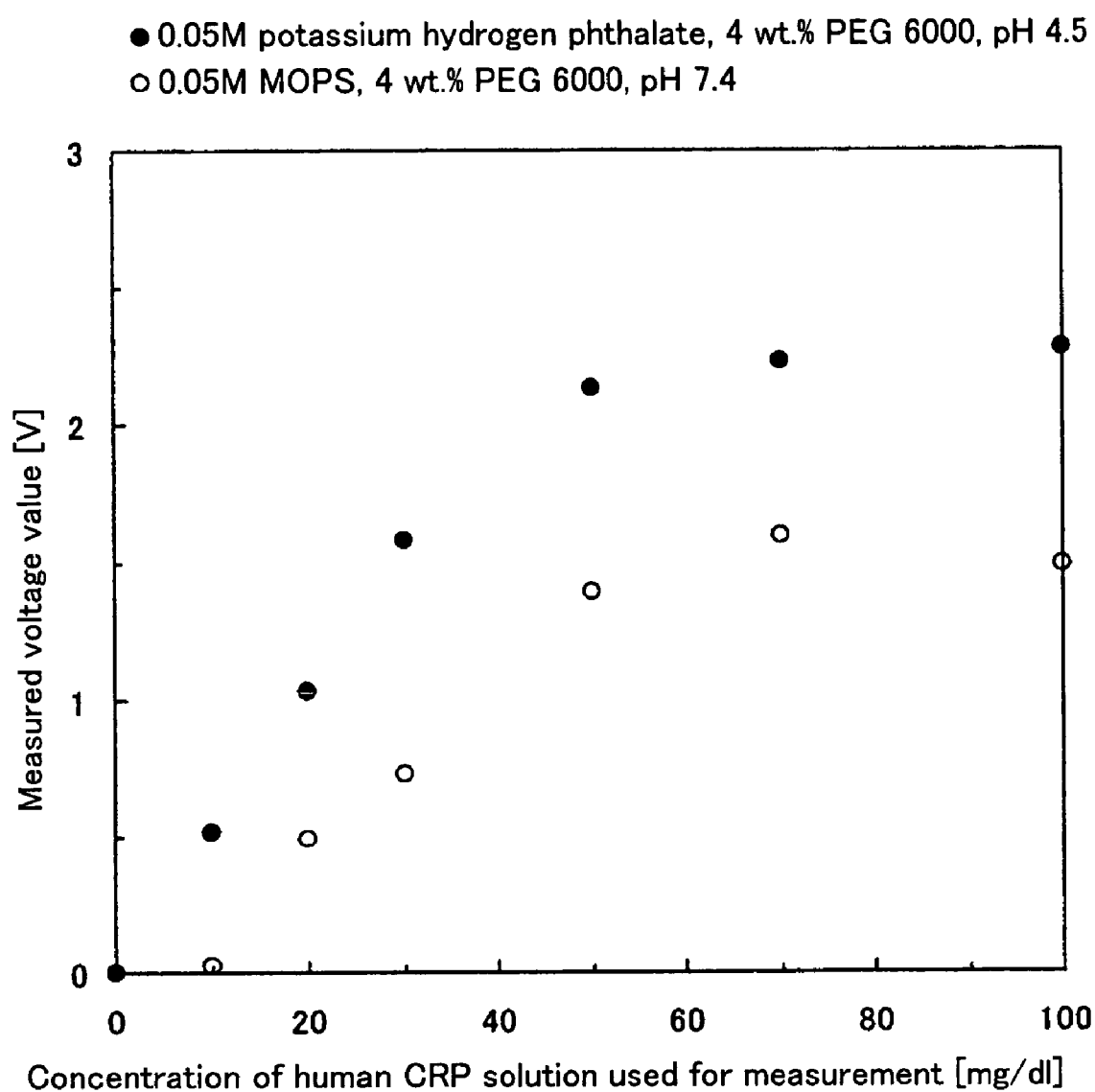
FIG. 10 is a graph showing the results of human CRP measurement by immunonephelometry, in an immunoreaction measurement method using a reagent kit for immunoreaction measurement including a mouse antihuman CRP monoclonal antibody and potassium hydrogen phthalate of yet another example of the present invention and in a comparative example.

The results are as follows. FIG. 10 is a view obtained by plotting the results of the measurement performed after the addition of the human CRP solutions having concentrations up to 100 mg/dl to the 0.05 M potassium hydrogen phthalate buffer solution prepared in Example 2 using potassium hydrogen phthalate as the phthalic acid or phthalate salt and the 0.05 M MOPS buffer solution as the comparative example. The Y-axis represents the measured voltage value and the X-axis represents the concentration of the human CRP solution used for the measurement. Each of the plotted values is a value obtained by subtracting the value measured when the human CRP concentration is 0 mg/dl from the measured value for the human CRP solution having each concentration. The reading of the graph is the same as that in FIG. 9.

From FIG. 10, it was found that in the human CRP measurement using the 0.05 M MOPS buffer solution as the comparative example, a sufficient difference was not obtainable between the measured value for the 10 mg/dl human CRP solution and that for the 0 mg/dl human CRP solution, and thus measurement of a difference in human CRP concentration substantially failed. On the contrary, in the measurement using the 0.05 M potassium hydrogen phthalate buffer solution, evidently higher measured values were obtained for the human CRP solutions having the respective concentrations, and a sufficient difference was obtainable between the measured value for the 10 mg/dl human CRP solution and that for the 0 mg/dl human CRP solution. That is, measurement of a difference in human CRP concentration was possible.

As described in Examples 7 and 8, it was confirmed that the immunoreaction measurement method and the reagent kit for immunoreaction measurement used for this method according to the present invention had also the effect of improving the measured value for the human CRP measurement.

As described above, in the immunoreaction measurement method and the reagent kit for immunoreaction measurement according to the present invention, phthalic acid or phthalate salt exists in a reaction system for immunoreaction, and the reaction system has an acidic pH. Therefore, the measured value of the immunoreaction due to antigen-antibody binding can be improved, and also the zone phenomenon occurring in an antigen-excess region can be eased.

In the conventional method in which a water soluble polymer is added, it is necessary to add a water soluble polymer in a high concentration or a water soluble polymer having a high molecular weight, to improve the measured value, maintain a good S/N ratio and ensure stable measurement. This causes a problem of increasing the viscosity of the solution and thus making handling of the solution during analysis operation difficult. According to the present invention, however, since phthalic acid or phthalate salt is a low molecular-weight substance, the viscosity of the solution is not increased, and thus handling of the solution during measurement operation is easy.

In addition, in the immunoreaction measurement method and the reagent kit for immunoreaction measurement according to the present invention, since the zone phenomenon is eased, drop of the measured values for high concentrations of the subject substance is reduced. This enables widening of the measurable concentration range within which the content of the subject substance can be measured precisely.

INDUSTRIAL APPLICABILITY

As described above, according to the present invention, an immunoreaction measurement method capable of improving the measured value easily, and a reagent kit for immunoreaction measurement used for this method, can be provided. In addition, an immunoreaction measurement method capable of easing the zone phenomenon occurring in an antigen-excess region, and a reagent kit for immunoreaction measurement used for this method, can be provided.

The invention claimed is:

1. An immunoreaction measurement method for measuring the content of a subject substance in a sample through optical measurement, comprising the steps of:
   (A) constructing a reaction system including the sample containing said subject substance, a specific-binding substance specifically binding to the subject substance and phthalic acid or phthalate salt; and
   (B) measuring an optical property of the reaction system, wherein in the step (A), the pH of the reaction system is set in a range of 4.5 to 5.5
   and the subject substance and the specific-binding substance is a combination of an antigen and an antibody, and
   in the step (B), a degree of turbidity of the reaction system is measured.

2. The immunoreaction measurement method of claim 1, wherein the optical property is a scattered light intensity or a transmitted light amount.

3. The immunoreaction measurement method of claim 1, wherein in the step (A), the reaction system further includes a buffering agent.

4. The immunoreaction measurement method of claim 1, wherein in the step (A), the concentration of the phthalic acid or phthalate salt in the reaction system is 0.2 M or less.

5. The immunoreaction measurement method of claim 1, wherein the phthalate salt is potassium hydrogen phthalate.

6. The immunoreaction measurement method of claim 1, wherein the reaction system includes 2 to 6 wt. % polyethylene glycol.

7. The immunoreaction measurement method of claim 1, wherein the subject substance is an antigen having a structure which can hold metal ions inside, and
   the specific-binding substance is an antibody specifically binding to the antigen in a state that the metal ions have been released therefrom.

8. The immunoreaction measurement method of claim 7, wherein the subject substance is human C-reactive protein.

9. The immunoreaction measurement method of claim 1, wherein the subject substance is an antigen having a structure of holding metal ions inside,
   the specific-binding substance is a polyclonal antibody, and
   in the step (A), the reaction system further includes the metal ions.

10. The immunoreaction measurement method of claim 9, wherein the subject substance is human C-reactive protein.

11. The immunoreaction measurement method of claim 1, wherein the subject substance is an antigen, and
   the specific-binding substance is a monoclonal antibody capable of binding to a plurality of binding sites of the antigen.

12. The immunoreaction measurement method of claim 11, wherein the subject substance is human C-reactive protein.

* * * * *

UNITED STATES PATENT AND TRADEMARK OFFICE
CERTIFICATE OF CORRECTION

PATENT NO. : 7,056,682 B2
APPLICATION NO. : 10/474755
DATED : June 6, 2006
INVENTOR(S) : Akihito Kamei et al.

It is certified that error appears in the above-identified patent and that said Letters Patent is hereby corrected as shown below:

On the title page of the Letters Patent;

Under section "(75) Inventors:", change:

" Akihito Kamei, Yawata (JP) " to -- Akihito Kamei, Kyoto (JP) --,
" Noriko Kenjyo, Hirakata (JP) " to -- Noriko Kenjyo, Osaka (JP) --,
" Tatsuhiko Kawamura, Kyotanabe (JP) " to -- Tatsuhiko Kawamura, Kyoto (JP) --,
"Mahito Hirai, Kyotanabe (JP) " to -- Mahito Hirai, Kyoto (JP) --

Signed and Sealed this

Thirteenth Day of February, 2007

JON W. DUDAS
*Director of the United States Patent and Trademark Office*

UNITED STATES PATENT AND TRADEMARK OFFICE
CERTIFICATE OF CORRECTION

PATENT NO. : 7,056,682 B2  Page 1 of 1
APPLICATION NO. : 10/474755
DATED : June 6, 2006
INVENTOR(S) : Akihito Kamei et al.

It is certified that error appears in the above-identified patent and that said Letters Patent is hereby corrected as shown below:

On the title page of the Letters Patent;

Under section "(56) References Cited, U.S. PATENT DOCUMENTS", add
-- 5,420,016  05/1995  Boguslaski et al. --

Signed and Sealed this

Thirtieth Day of October, 2007

JON W. DUDAS
*Director of the United States Patent and Trademark Office*